US007216665B1

(12) United States Patent
Sims, Jr.

(10) Patent No.: US 7,216,665 B1
(45) Date of Patent: May 15, 2007

(54) RETRACTABLE REEL

(75) Inventor: Dewey Sims, Jr., Berkley, MI (US)

(73) Assignee: Sub-Q, LLC, Wayne, MI (US)

( * ) Notice: Subject to any disclaimer, the term of this patent is extended or adjusted under 35 U.S.C. 154(b) by 141 days.

(21) Appl. No.: 10/872,279

(22) Filed: Jun. 18, 2004

(51) Int. Cl.
*A62C 35/00* (2006.01)
*B65H 75/34* (2006.01)

(52) U.S. Cl. .................. 137/355.19; 137/355.26; 206/389; 239/52; 242/596.4; 604/890.1

(58) Field of Classification Search ............ 604/890.1, 604/891.1, 159; 137/335.12, 335.19, 335.26, 137/335.16; 206/389; 239/52; 242/596.4
See application file for complete search history.

(56) References Cited

U.S. PATENT DOCUMENTS

| | | | |
|---|---|---|---|
| 1,446,410 A * | 2/1923 | Hudson et al. .......... 242/378.2 |
| 4,384,688 A | 5/1983 | Smith | |
| 5,094,396 A * | 3/1992 | Burke ..................... 242/378.2 |
| 5,422,957 A | 6/1995 | Cummins | |
| 5,684,883 A * | 11/1997 | Chen ......................... 381/385 |
| 6,019,304 A * | 2/2000 | Skowronski et al. ....... 242/373 |
| 6,065,490 A | 5/2000 | Falcone, Jr. | |
| 6,199,784 B1 * | 3/2001 | Wang et al. ................ 242/378 |
| 6,446,898 B1 * | 9/2002 | Hwang .................... 242/378.1 |
| 6,497,378 B1 * | 12/2002 | Liao ....................... 242/378.1 |
| RE38,211 E * | 8/2003 | Peterson et al. ........... 242/373 |
| 6,616,080 B1 * | 9/2003 | Edwards et al. ......... 242/378.1 |

(Continued)

FOREIGN PATENT DOCUMENTS

WO  WO-03/057028  7/2003

*Primary Examiner*—Kevin C. Sirmons
*Assistant Examiner*—Andrew Gilbert
(74) *Attorney, Agent, or Firm*—Mastrogiacomo PLLC; Patrick Mastrogiacomo, Jr.

(57) ABSTRACT

A retractable reel includes a housing having a front cover and a rear cover, the rear cover including a first opening and the front cover including a second opening, a trough extending radially inward from the second opening to a center of the front cover, the trough including at least one tab and at least one dimple and a resiliently deflectable latch arm. A spool includes a wall that extends axially outward from a front surface of the spool, the spool is rotatably supported within the housing and is positioned such that the front surface, the wall and the front cover cooperatively define a chamber therebetween. The spool further includes at least one ratchet member selectively engaged by the resiliently deflectable latch arm to prevent rotation of the spool in a winding direction. The retractable reel includes a spring having a first end engaging the rear cover and a second end engaging the spool for rotatively biasing the spool in the winding direction. The retractable reel also includes a flexible member having a first portion that passes through the first opening and is spirally wound upon the spool and a second position that passes through the second opening, the second portion having a first section secured to the housing in the trough by the tab and dimple, and a second section is spirally wound within the chamber. The first portion of the flexible member may be selectively unwound from the spool as the second portion of the flexible member is unwound and wound about itself within the chamber or wound upon the spool as the second portion of the flexible member is unwound and wound about itself within the chamber.

23 Claims, 21 Drawing Sheets

U.S. PATENT DOCUMENTS 6,694,922 B2 2/2004 Walter et al.
2003/0122021 A1* 7/2003 McConnell et al. ..... 242/388.1
2003/0146332 A1 8/2003 Vinding

* cited by examiner

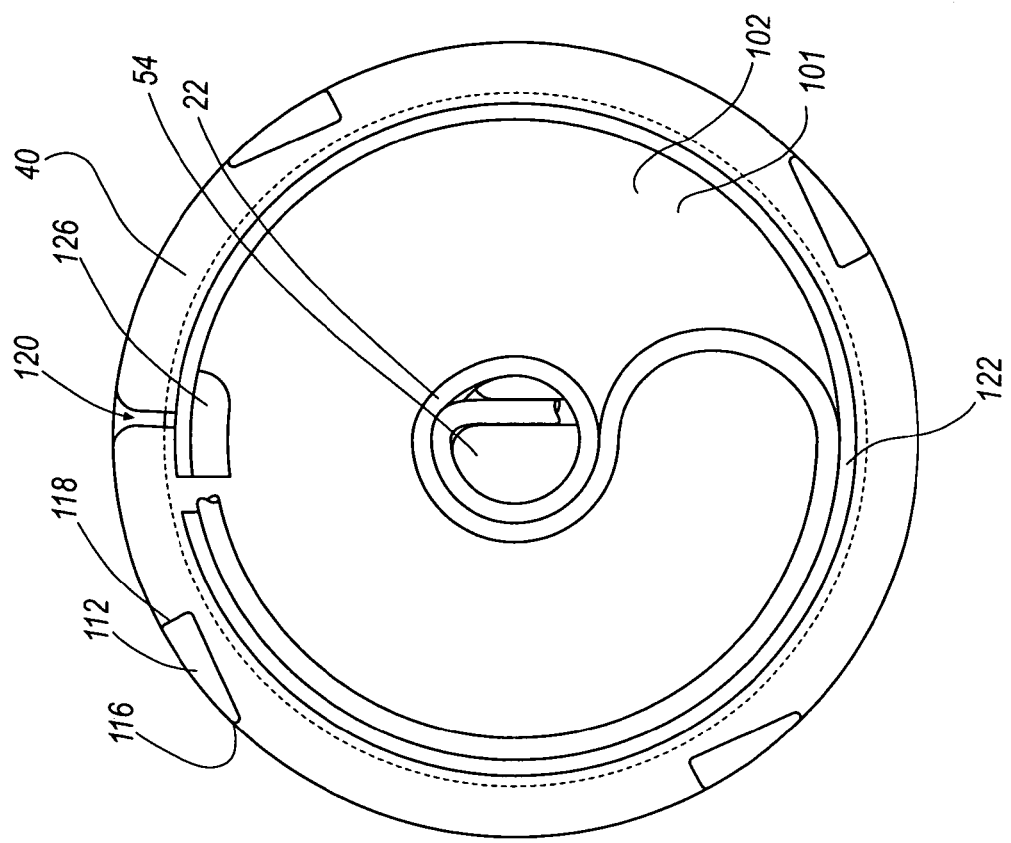
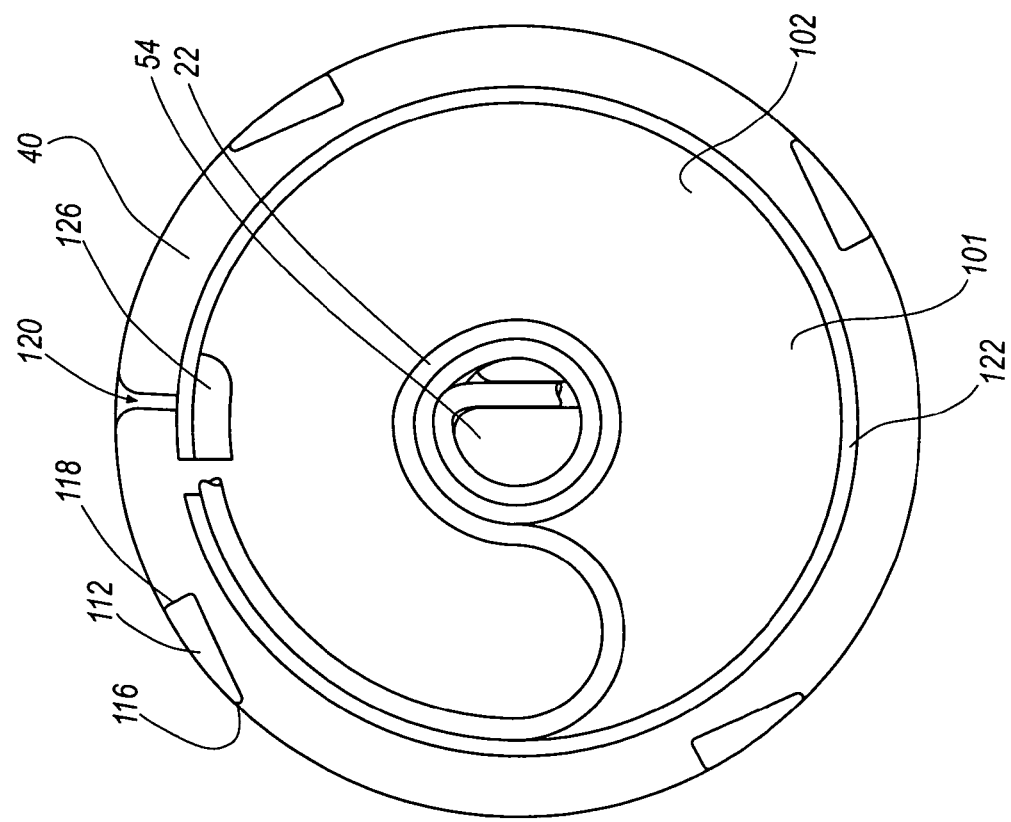

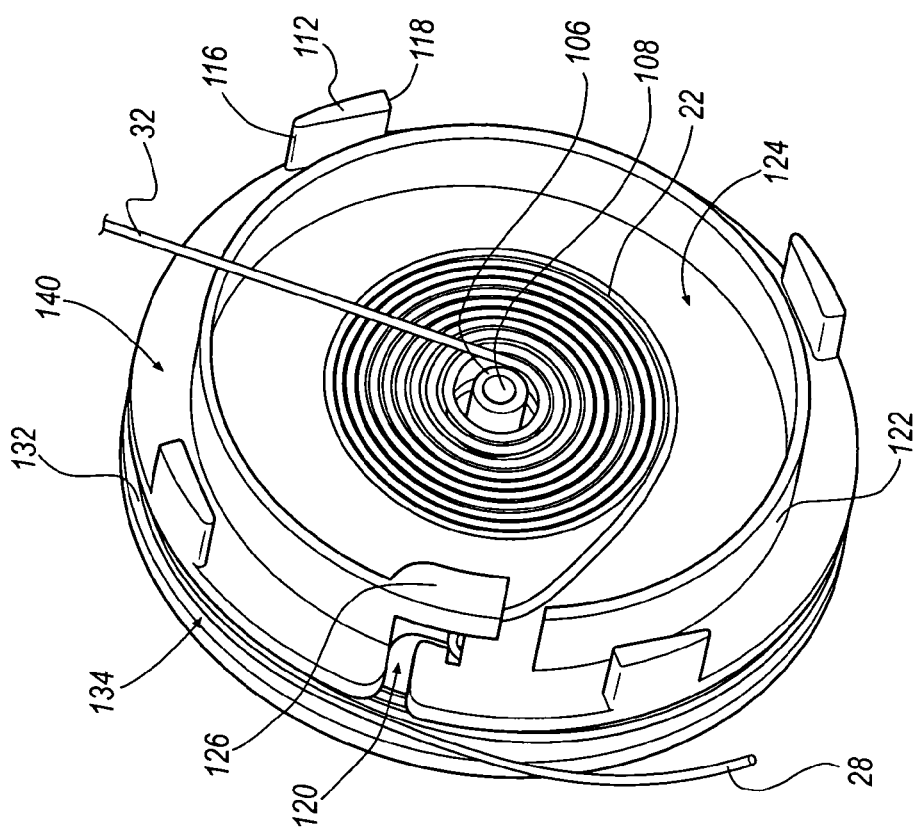
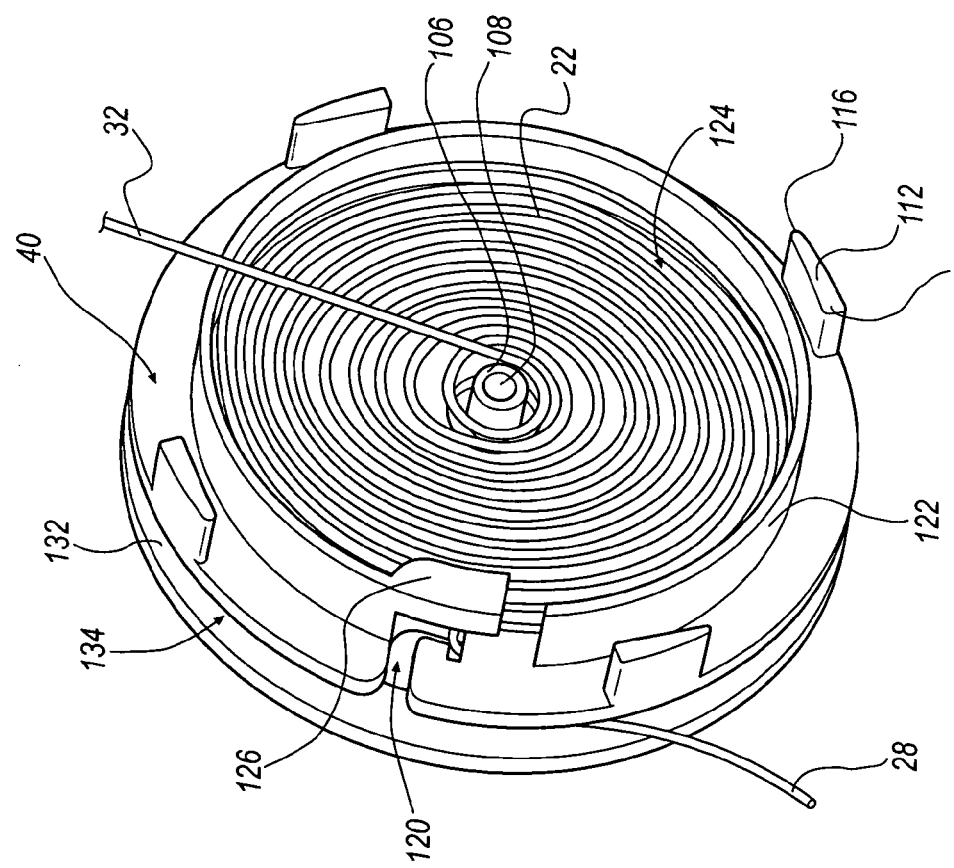
FIG. 10A
FIG. 10B

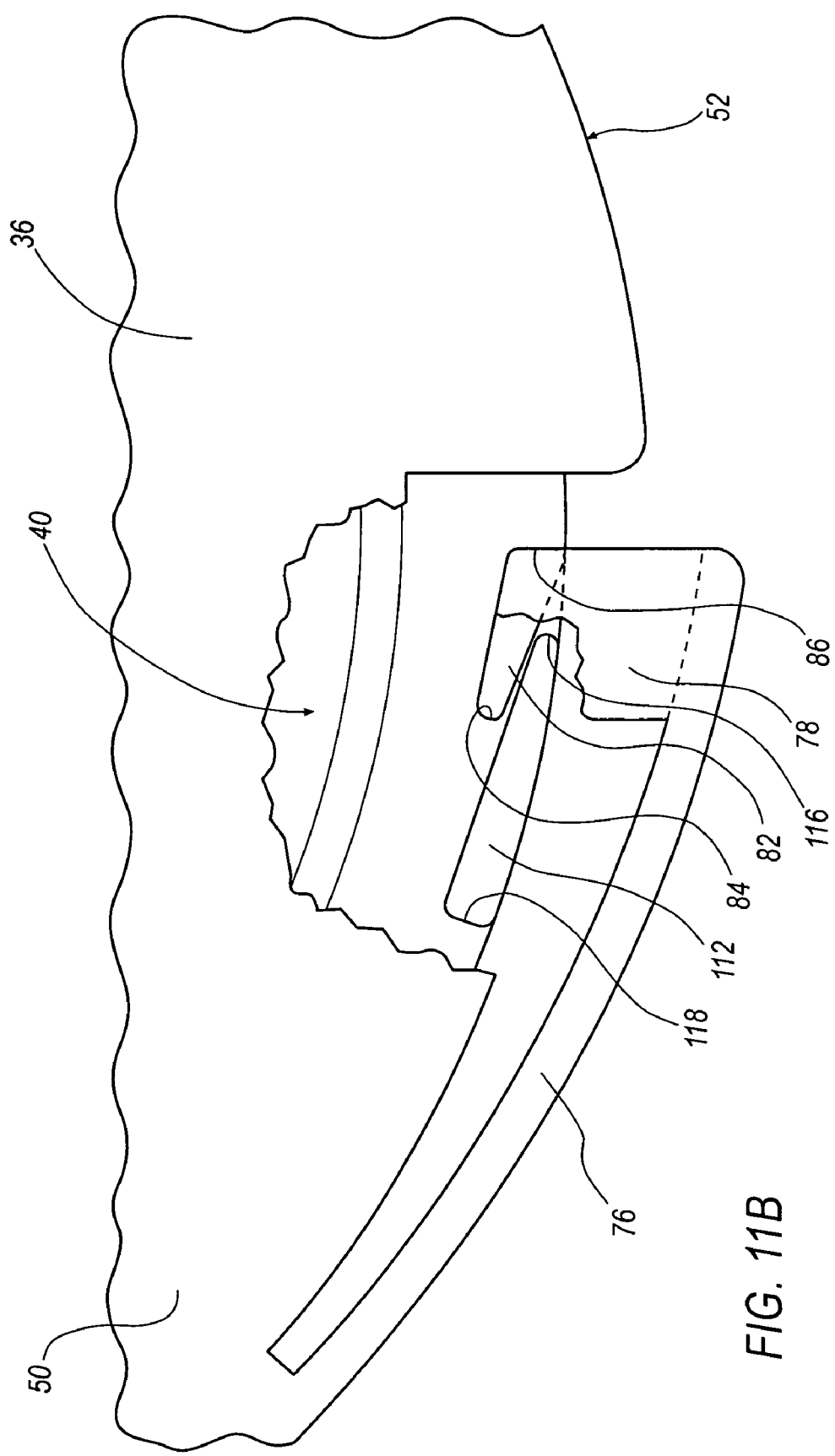

RETRACTABLE REEL

FIELD OF THE INVENTION

The present invention relates generally to a tube included in an infusion set used with an insulin pump and, more particularly, to a retractable reel for retracting, storing, and releasing the tube when needed.

BACKGROUND OF THE INVENTION

Diabetes is a widely known disease that affects a human body's ability to produce insulin. Insulin is produced and used by the human body to regulate blood glucose levels. If the human body does not produce adequate amounts of insulin, insulin must be introduced into the human body artificially. Insulin is commonly introduced into the human body by injection. Typically, the amount of insulin needed by the human body to regulate blood glucose levels determines how often an injection is required. If large amounts of insulin are needed by the human body, a diabetic patient will require a number of daily injections. To alleviate the requirement of multiple daily injections or to escape the need for injections altogether, an insulin pump can be utilized by the diabetic patient as a substitute for injections. Insulin pumps contain a supply of insulin that is pumped directly into the human body at a continuous level on an intermittent basis. The insulin pump normally supplies insulin to the human body through a tube. One end of the tube is attached to the insulin pump and the opposite end is attached to a needle or cannula that is inserted under the diabetic patient's skin, typically on the abdomen. An adhesive patch is placed over the area where the needle or cannula enters the skin and is used to ensure the needle or cannula remains in place under the skin. The tube, needle or cannula, and adhesive patch create a tubular assembly. The tubular assembly is commonly known as an infusion set.

Insulin pumps are small enough to be worn by diabetic patients under clothing and are typically clipped to a belt or waist band. At times, however, the insulin pump will have to be removed from the waist area. For example, because the amount of insulin needed by the human body is monitored by the diabetic patient, the diabetic patient needs to be able to read the output monitor of the insulin pump to ensure that the proper dose of insulin is being delivered. At the same time, the diabetic patient does not want to remove the needle or cannula from under the skin or disconnect the tube from the pump or needle or cannula in order to move the pump into a position to read the monitor. Conventional infusion sets include tubing of sufficient length to allow the diabetic patient to move the insulin pump to a comfortable reading location without disconnecting the tube from the insulin pump or needle or cannula. While there are occasions when the insulin pump must be removed from the patient's abdomen and the additional length of tube is required, much of the time the insulin pump is positioned at the diabetic patient's waist. The additional length of tube poses a potential hazard, as it can become snagged on objects around the home, office, etc., which may cause the needle or cannula to be removed from the patient. In an attempt to alleviate the problem of catching the tube on an object, a diabetic patient may coil the excess tube and keep the coiled tube close to the insulin pump. This coiling of the tube may lead to kinks in the tube, causing an interruption in the flow of insulin.

Therefore, a need exists for a retractable reel that can be used with the tube of an infusion set and an insulin pump to ensure that excess tube can be stored securely. The secure storage of the excess tube will help to alleviate the possibility of catching the excess tube on an object as well as prevent a tube from becoming kinked or otherwise damaged in a way that would compromise the flow of insulin into the patient' body.

SUMMARY OF THE INVENTION

A retractable reel is provided that includes a housing having a front cover and a rear cover, the rear cover including a first opening and the front cover including a second opening, a trough extending radially inward from the second opening to a center of the front cover, the trough including at least one tab and at least one dimple, and a resiliently deflectable latch arm. A spool includes a wall that extends axially outward from a front surface of the spool, the spool is rotatably supported within the housing and is positioned such that the front surface, the wall, and the front cover cooperatively define a chamber therebetween. The spool further includes at least one ratchet member selectively engaged by the resiliently deflectable latch arm to prevent rotation of the spool in a winding direction. The retractable reel includes a spring having a first end engaging the rear cover and a second end engaging the spool for rotatively biasing the spool in the winding direction. The retractable reel also includes a flexible member having a first portion that passes through the first opening and is spirally wound upon the spool and a second portion that passes through the second opening, the second portion having a first section secured to the housing in the trough by the tab and the dimple and a second section spirally wound within the chamber. The first portion of the flexible member may be selectively unwound from the spool as the second portion of the flexible member is unwound and wound about itself within the chamber or wound upon the spool as the second portion of the flexible member is unwound and wound about itself within the chamber. A medical system that includes an insulin pump and a retractable reel according to the present invention is also disclosed.

BRIEF DESCRIPTION OF THE DRAWINGS

The features and inventive aspects of the present invention will become more apparent upon reading the following detailed description, claims, and drawings, of which the following is a brief description:

FIGS. 8A, 8B, 8C, 8D, and 8E are detailed plan views of the spool and a flexible member according to an embodiment of the present invention shown in different states of extraction and retraction;

FIGS. 10A and 10B are perspective views of the spool and the flexible member according to another embodiment of the present invention shown in the extracted and retracted states respectively.

FIGS. 11A, 11B, and 11C are detailed views of the front cover and the spool according to an embodiment of the present invention.

DETAILED DESCRIPTION

Figure 1:
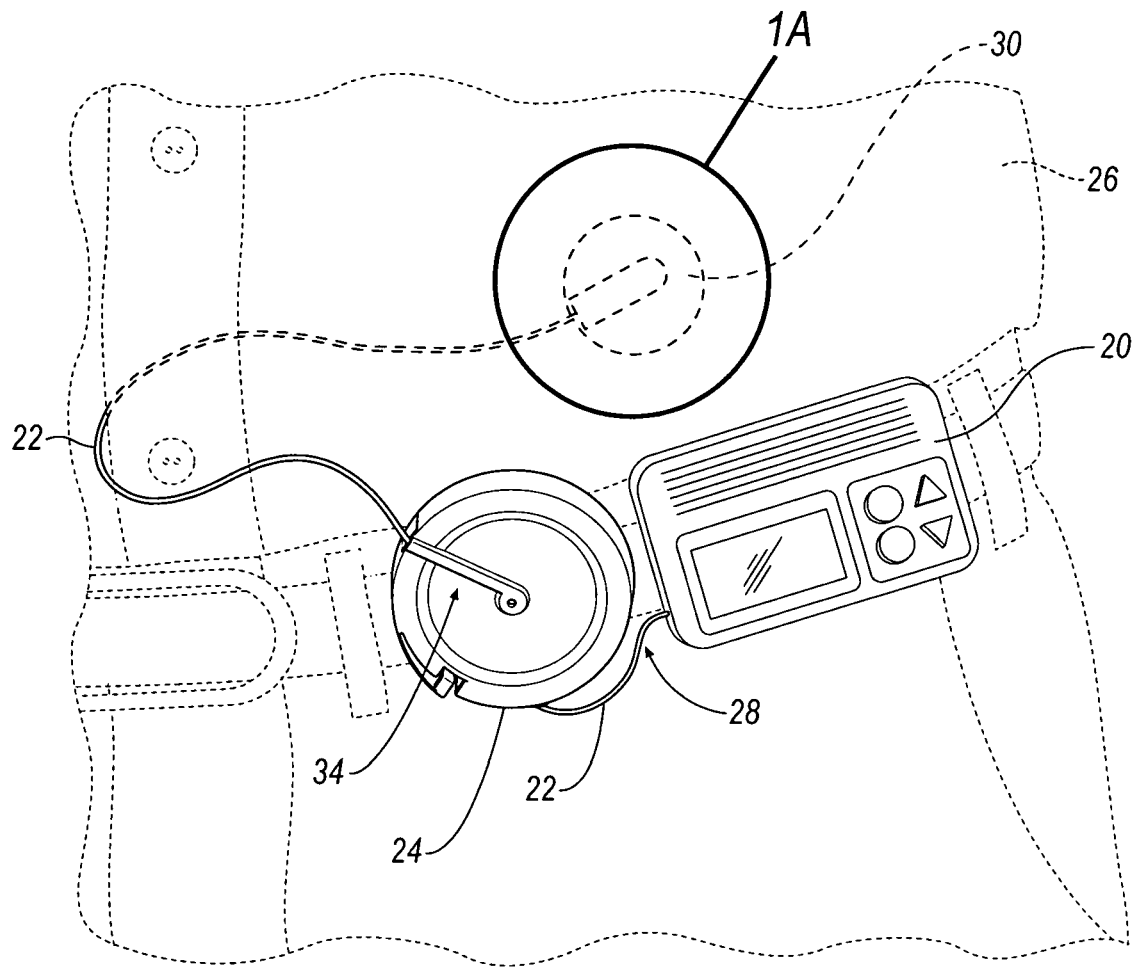
FIG. 1 is a perspective view of a medical system, including a retractable reel and an insulin pump, attached to a diabetic patient according to an embodiment of the present invention.
Figure 1A:
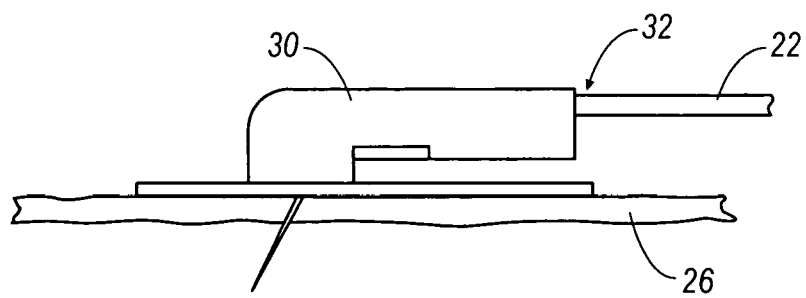
FIG. 1A is a side elevational view of a needle or cannula for use in the medical system of FIG. 1.

Referring to FIGS. 1 and 1A, a medical system including an insulin pump 20 for diabetic therapy in cooperation with a tube 22 and a retractable reel 24 is shown according to an embodiment of the invention. Insulin pump 20 is attached to a diabetic patient 26 by tube 22, which is used to transfer a predetermined amount of insulin from insulin pump 20 to diabetic patient 26. Tube 22 is connected to insulin pump 20 at a first tubular end 28 and to diabetic patient 26, through a needle or cannula member 30, at a second tubular end 32. Needle or cannula 30 is inserted into patient's 26 skin and held in place with the aid of an adhesive patch or strips (not shown).

Normally, insulin pump 20 is positioned at the waist of diabetic patient 26; however, diabetic patient 26 may be required to monitor insulin pump 20 periodically to adjust for changes in blood glucose levels. Therefore, tube 22 must be long enough to permit diabetic patient 26 to position insulin pump 20 in a readable location. The excess length of tube 22 required to position insulin pump 20 for comfortable reading, poses a hazard to diabetic patient 26 when insulin pump 20 is positioned for normal operation at the waist because excess tube 22 may become caught on objects or kinked.

In an embodiment, retractable reel 24 is configured to take-up and encase at least a portion of tube 22 when not in use by diabetic patient 26 to locate insulin pump 20 in a readable location. By encasing a portion of tube 22 in retractable reel 24, tube 22 will be less likely to kink or become snagged on objects, thus ensuring an uninterrupted flow of insulin to diabetic patient 26. Retractable reel 24 may be utilized with any number of insulin pumps such as, but not limited to, the insulin pumps manufactured by Medtronic, Animas, Dana, Deltec, Disetronic, or Nipro.

Referring to FIGS. 1–7D, retractable reel 24 of the present invention will be described in greater detail. In an embodiment, retractable reel 24 includes tube 22 and a housing 34 having a front cover 36 and a rear cover 38. A spool 40 is positioned between front and rear covers 36, 38 of housing 34 and is biased by a spring 42 in one of two rotational directions. Reel device 24 may also include a clip 46 for attaching retractable reel 24 to another object, such as a belt worn by diabetic patient 26.

As shown in FIGS. 2, 3A, 3B, 7A, 7B, 7C, and 7D, front cover 36 includes a radially extending wall 51, having an interior surface 48, and an exterior surface 50, and an axially extending wall 52 that extends generally perpendicular from wall 51. A first hub 54 extends axially outward from wall 51 and includes a first hole 56 therethrough. A trough 58 extends radially inward from side wall 52 through interior surface 48 and first hub 54. Trough 58 is angled slightly from side wall 52 to avoid passing through first hole 56. Trough 58 may be sized to snugly hold tube 22 and, when so configured, may include dimples 60 to prevent tube 22 from moving axially within trough 58 and a lock 62 to prevent tube 22 from escaping trough 58 and interfering with tube 22 during operation of retractable reel 24 (See FIGS. 7B, 7C, and 7D). Top portion of dimples 60 are conically shaped to allow for a lower push in force when tube 22 is pressed into trough 58. Trough 58 further includes a ramp 64 to direct tube 22 onto interior surface 48. The walls of trough 58 that exits first hub 54 at ramp 64 are curved so as not to damage tube 22 as tube 22 is directed onto interior surface 48.

Figure 7A:
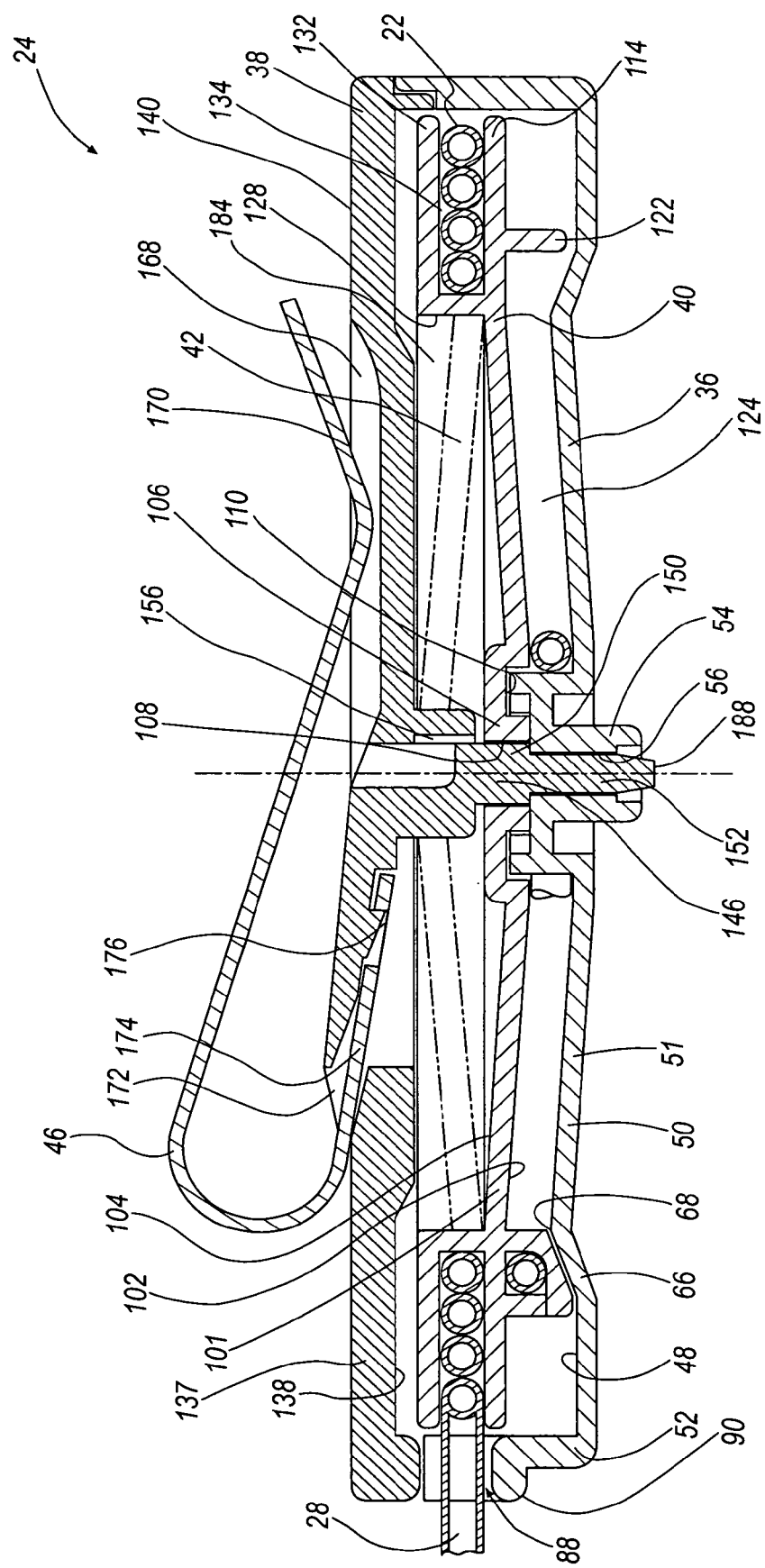
FIG. 7A is a cross-sectional view of the retractable reel according to an embodiment of the present invention.
Figure 7B:
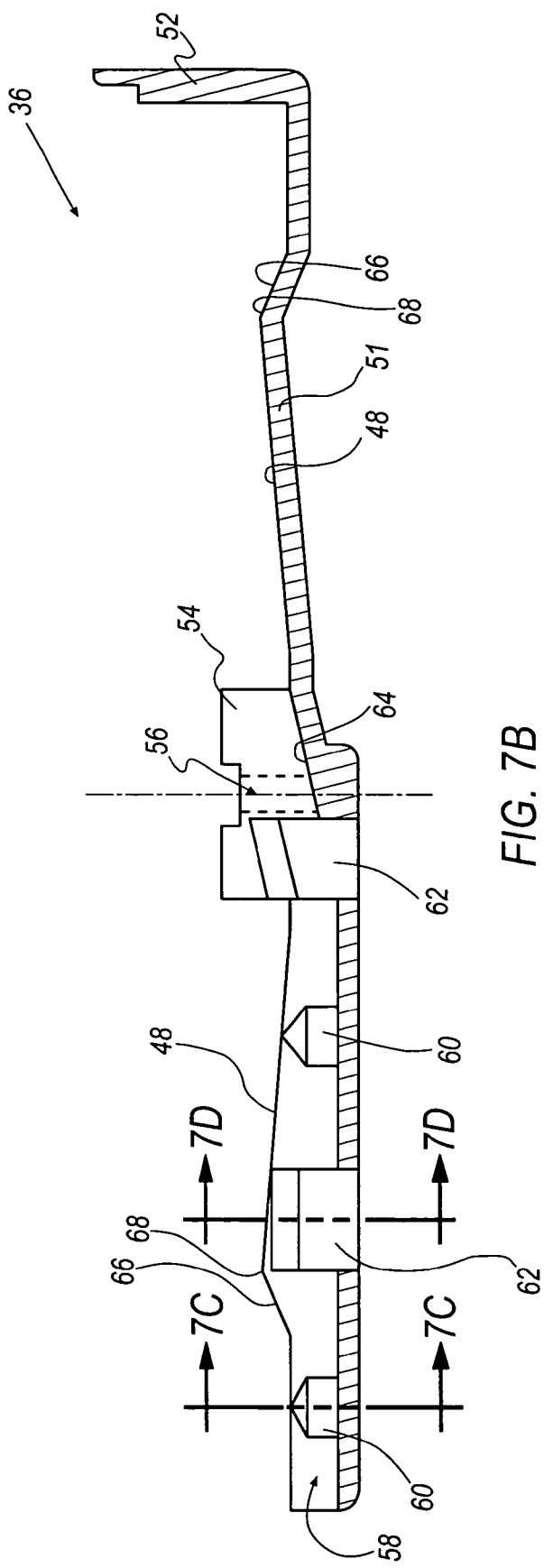
FIG. 7B is a cross-sectional view of the front cover according to an embodiment of the present invention.
Figure 7D:
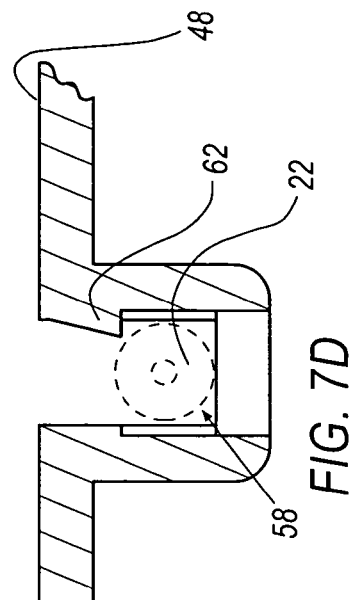
FIGS. 7C and 7D are cross-sectional views of a trough according to an embodiment of the present invention.
Figure 7C:
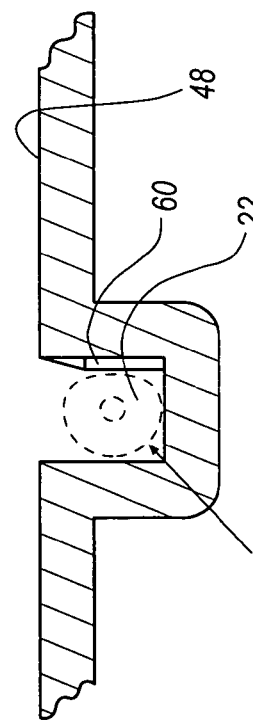
Figure 8D:
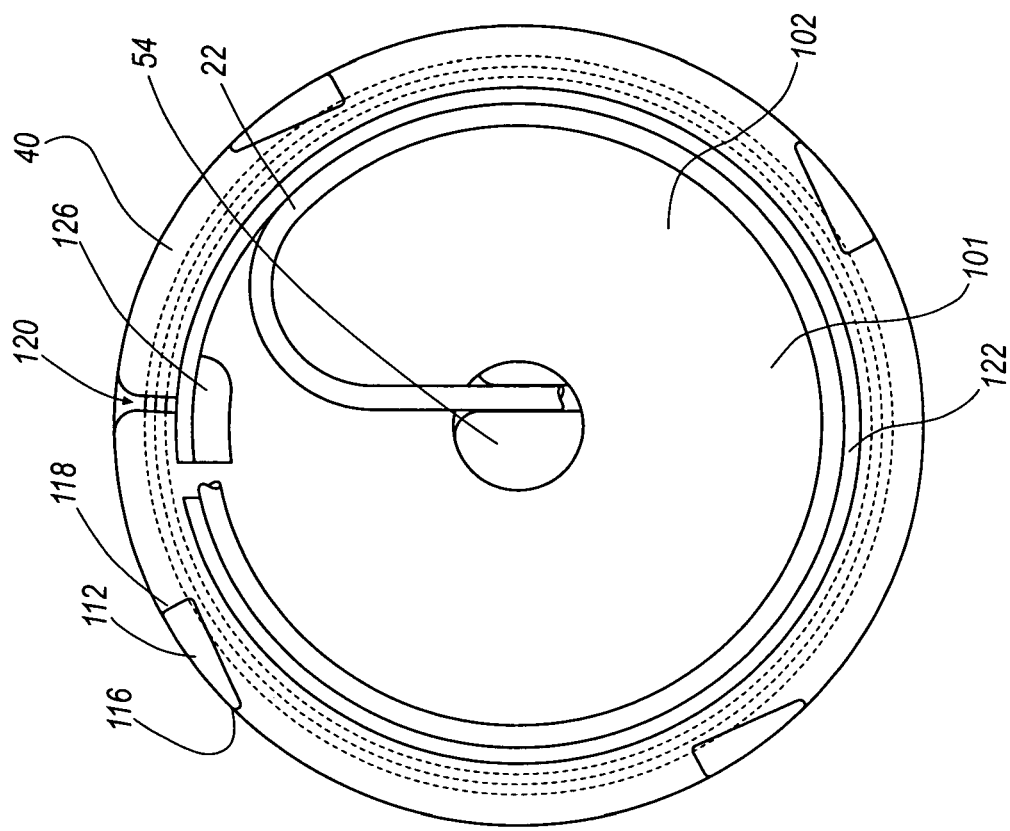
Figure 8C:
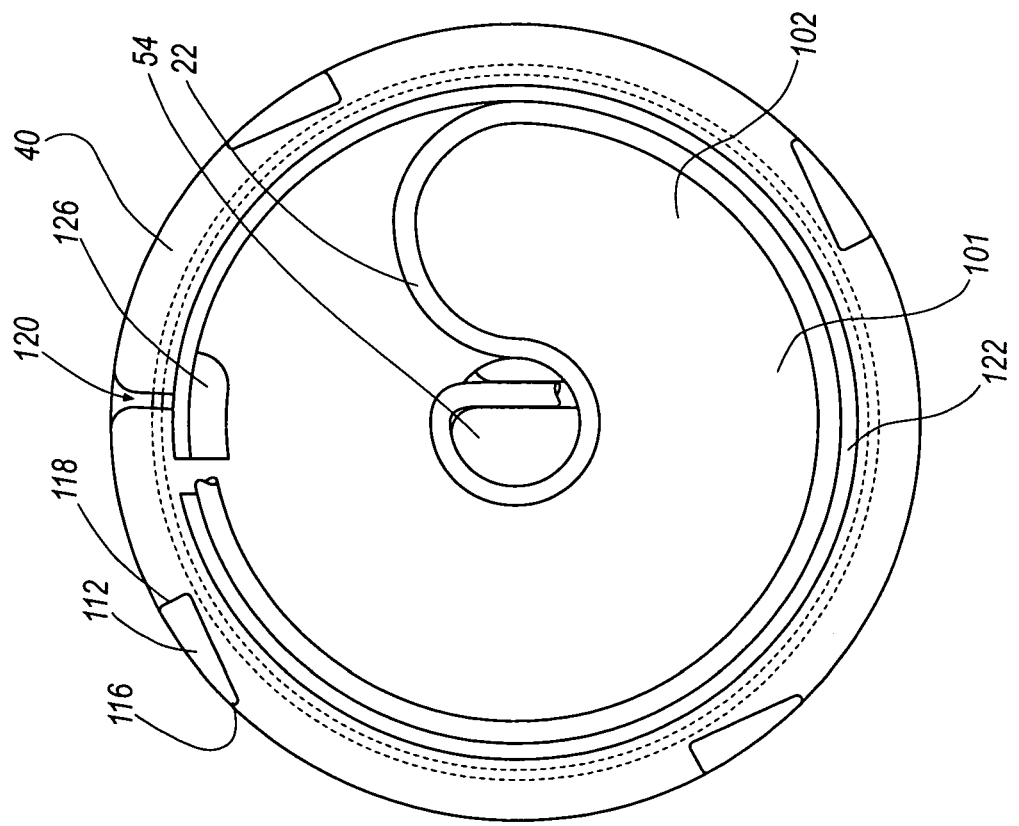
Figure 8E:
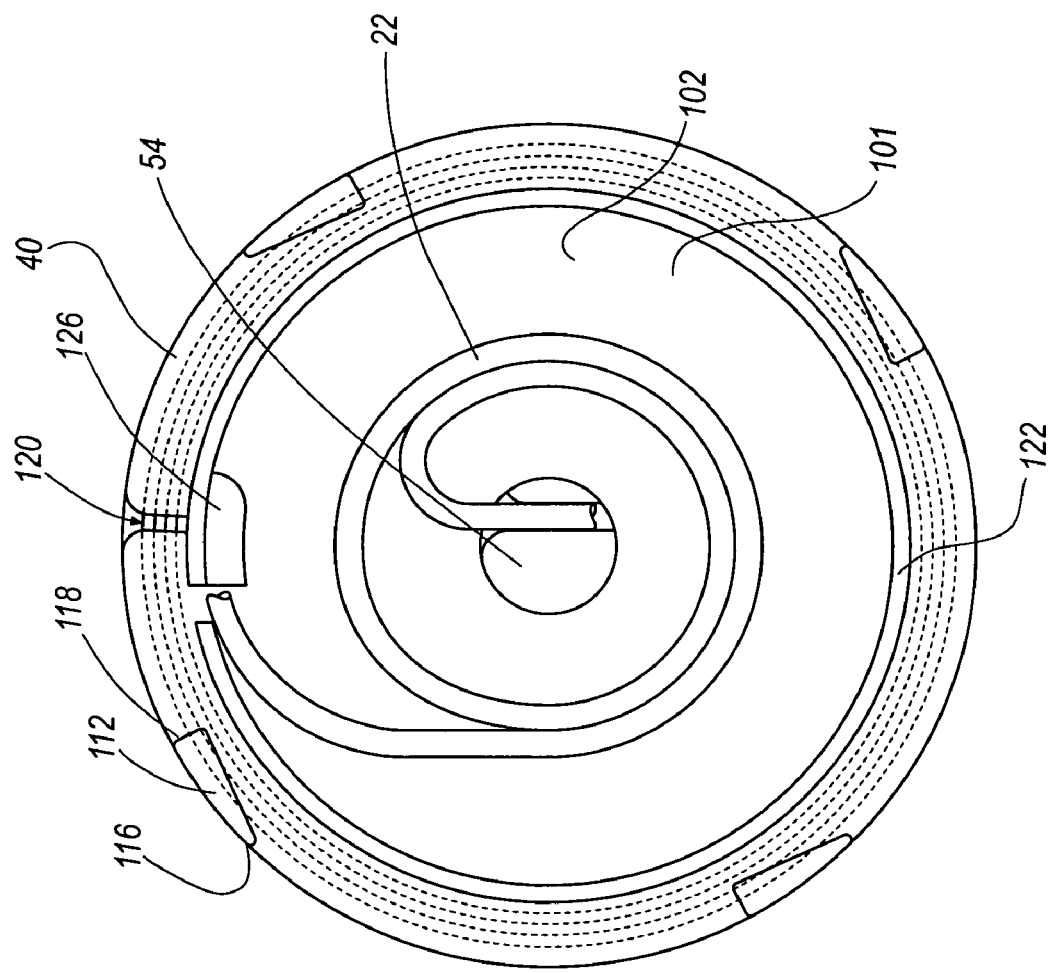
Figure 9A:
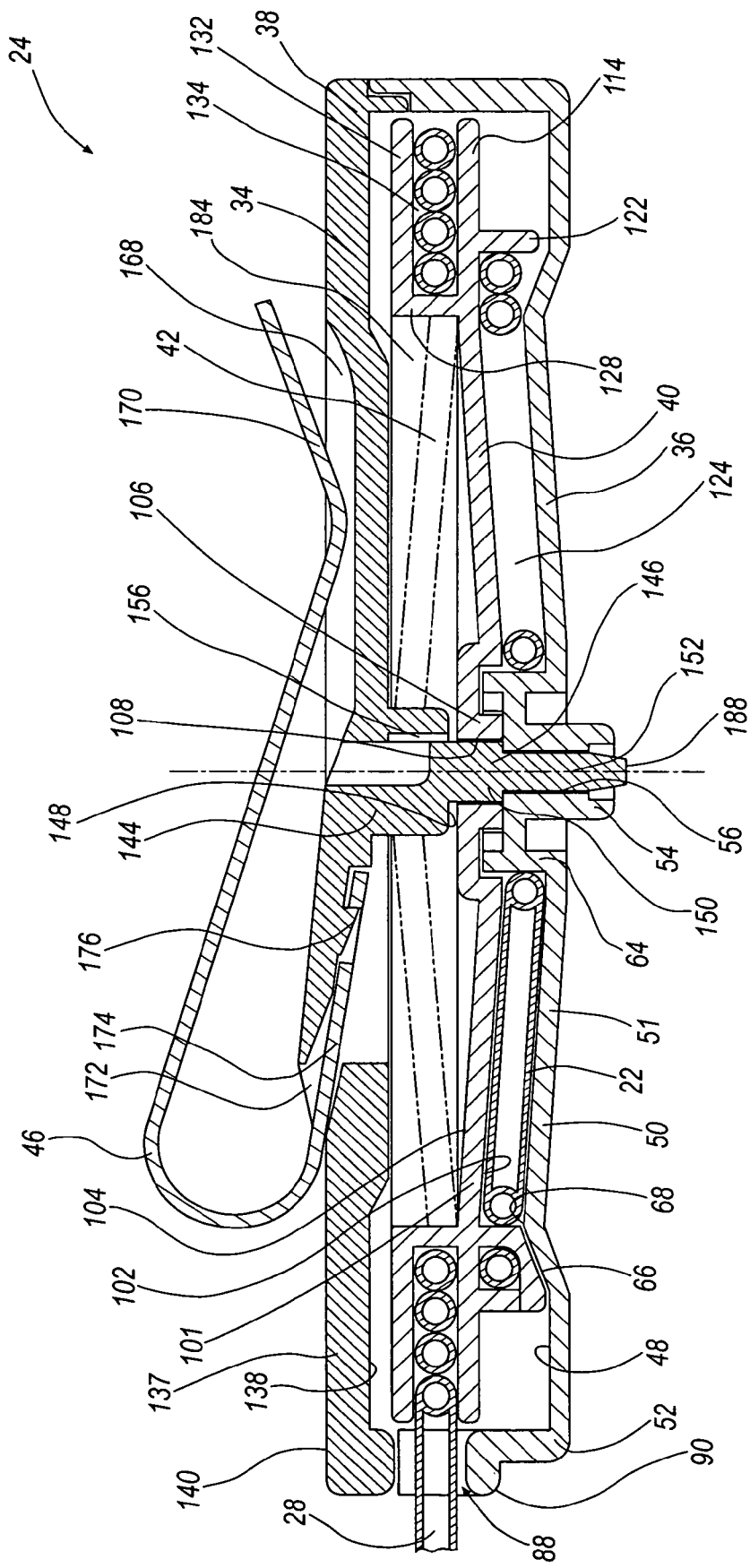
FIGS. 9A and 9B are cross-sectional views of the retractable reel according to another embodiment of the present invention.
Figure 9B:
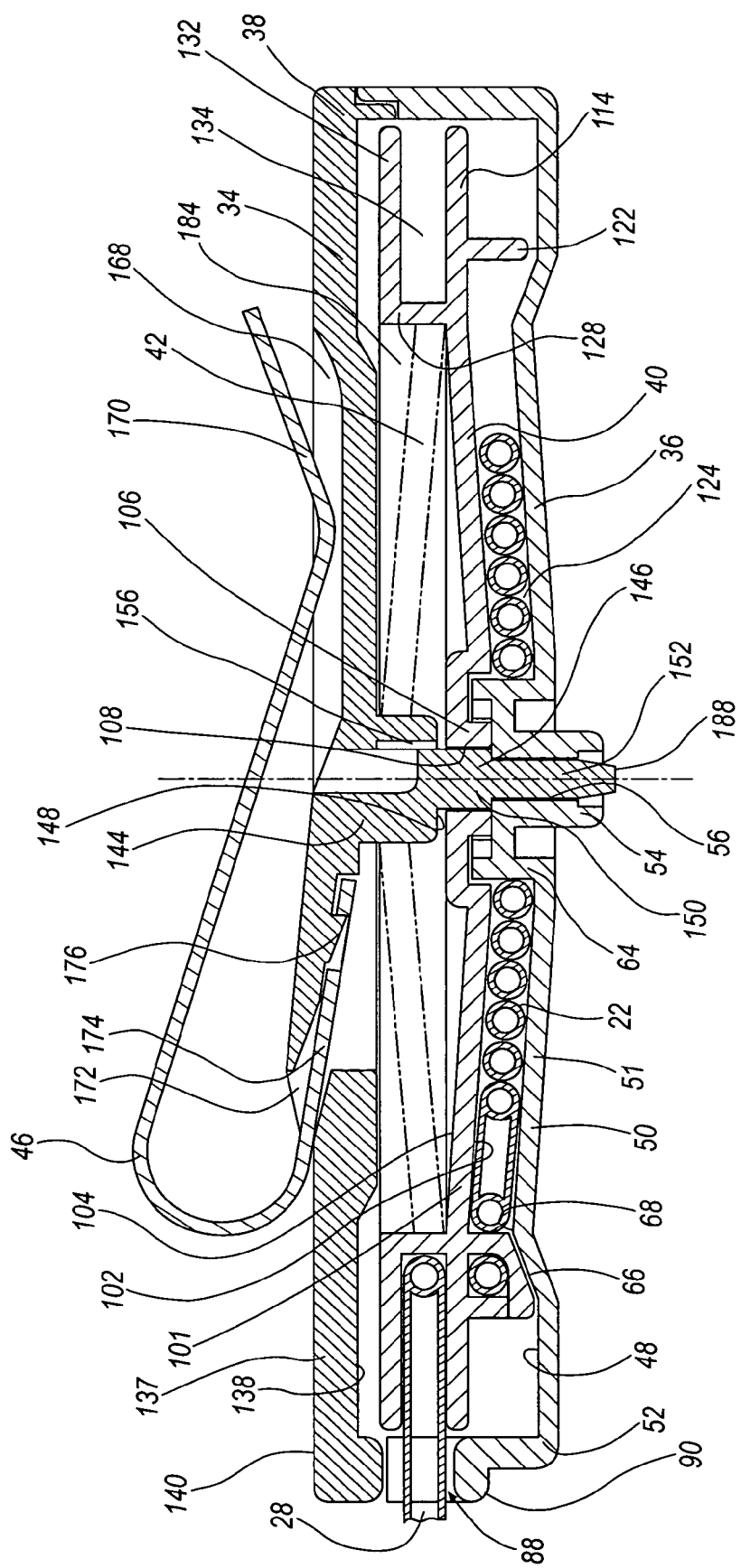

As shown in FIGS. 7A and 7B, radially extending wall 51 includes a chamfer 66 that extends axially outward from interior surface 48. Wall 51 is angled radially inward from an edge 68 of chamfer 66 toward first hub 54. Chamfer 66 allows for the inward angling of interior surface 48 toward first hub 54 to help ensure uniform winding and safe storage of tube 22 as tube 22 is wound about first hub 54. The uniform winding and safe storage of tube 22 will aid in preventing tube 22 from becoming kinked or entangled.

Exterior surface 50 of wall 51 includes an arcuate surface 70 that extends radially inward from side wall 52 through exterior surface 50 and first hub 54. Arcuate surface 70 provides a localized area of increased material on exterior surface 50 to allow trough 58 to run below interior surface 48 so that tube 22 can be held snugly in position. First hole 56 includes a countersink 72 that extends axially inward toward exterior surface 50.

Wall 51 also includes a notch 74 that provides clearance for a resiliently deflectable cantilever latch arm 76 of side wall 52. In an embodiment, latch arm 76 includes a tab 78 and a locking post 82 that extends axially from a radially inner portion of tab 78. In the illustrated embodiment, locking post 82 is generally triangular in shape having a pointed end 84 that expands to a wider end 86. Tab 78 and locking post 82 are configured to pass into and out of notch 74 when latch arm 76 is deflected radially inward toward first hub 54. As shown in FIG. 11C, latch arm 76 and front cover 36 are configured, such that when latch arm 76 is deflected radially inward toward first hub 54, latch arm 76 will contact front cover 36 preventing latch arm 76 from moving too far inward. As will be appreciated, in this particular embodiment, the width of latch arm 76 will be almost as wide as retractable reel 24 itself making retractable reel 24 easy to operate for small children or patients 26 with large fingers. Also, latch arm 76 may exhibit a relatively low spring rate to allow diabetic patients 26 with weak fingers to operate retractable reel 24. Finally, the design of latch arm 76 ensures that there will not be a continuous pulling force at the site where needle or cannula 30 enters diabetic patient 26. Even a small pulling force could loosen the adhesive patch that protects the site and dislodge needle or cannula 30.

Side wall 52 also includes a "C"-channel 88 to allow tube 22 to enter and exit housing 34. An arcuate surface 90 extends radially outward from side wall 52 and at least partially surrounds "C"-channel 88. Arcuate surface 90 provides a smooth surface for tube 22 to travel upon as tube 22 is extracted from or retracted into housing 34. Tube 22 enters housing 34 through an opening 92 in side wall 52 and is pressed into trough 58 to limit movement of tube 22 during operation of retractable reel 24. At opening 92, side wall 52 includes a first pair of stepped surfaces 94 that face radially outward. Opening 92 and stepped surfaces 94 are sized to accept a first tab 96 on rear cover 38. Side wall 52 further includes a shoulder 98 sized to receive a lip 100 included on rear cover 38.

FIGS. 2, 4A, 4B, and 7A illustrate spool 40 according to an embodiment of the invention. Spool 40 includes a radially extending wall 101 having a front surface 102 and a rear surface 104. Spool 40 includes a second hub 106 extending radially outward from front surface 102 of wall 101 and includes a second hole 108 passing through second hub 106 and rear surface 104. Front surface 102 includes a groove 110 that surrounds second hub 106 and provides clearance for first hub 58 when spool 40 rotates in housing 34. Front surface 102 also includes at least one ratchet member 112 that extends axially outward from front surface 102, proximate an outer edge 114 of spool 40. In the illustrated embodiment, spool 40 employs four ratchet members 112, which are generally triangular in shape and equally spaced about front surface 102. Ratchet members 112 include a pointed end 116 and a wider end 118. Ratchet members 112 are positioned to deflect or engage locking post 82 depending on the rotating direction of spool 40.

Figure 4A:
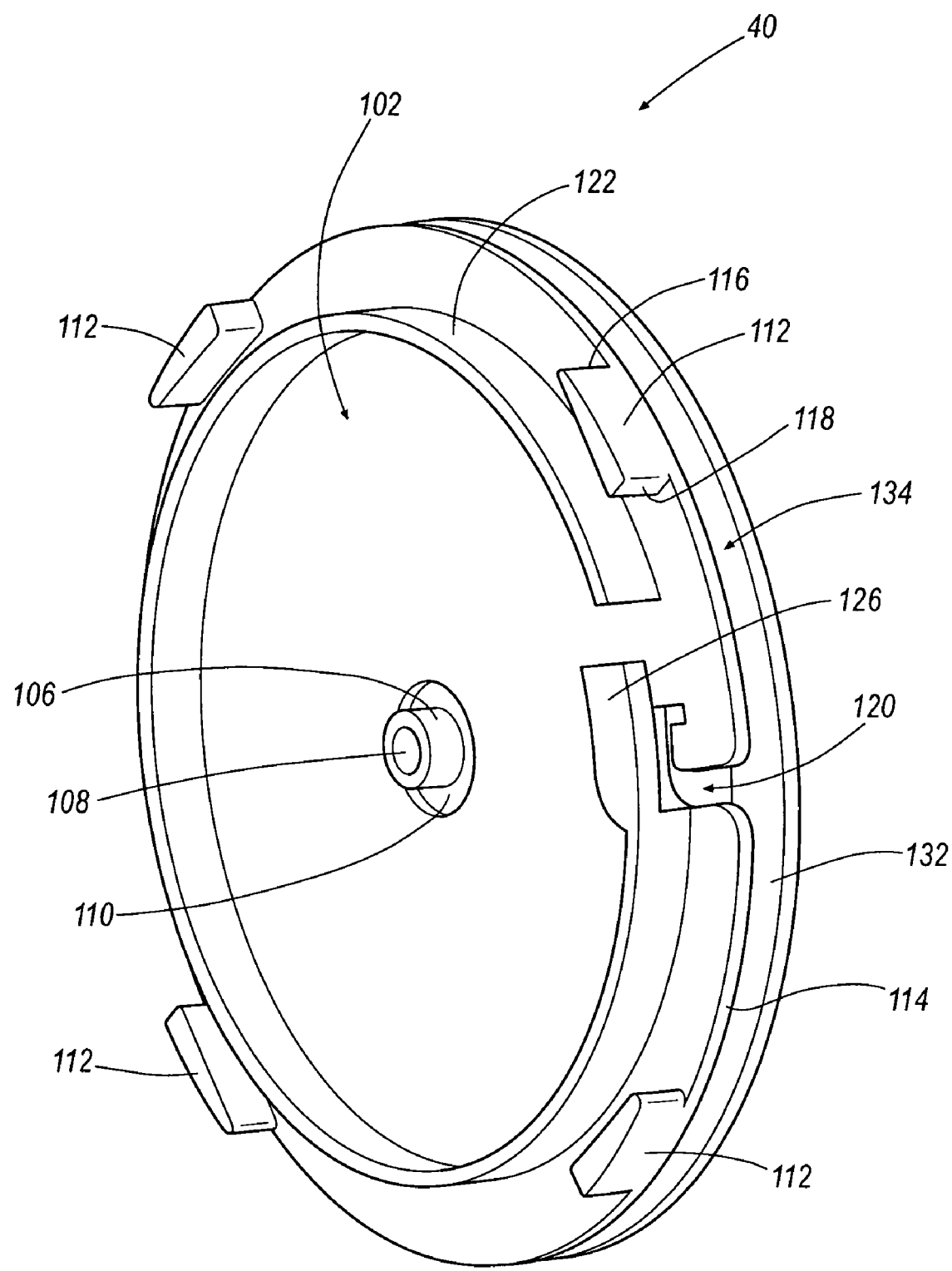
FIGS. 4A and 4B are perspective views of a spool according to an embodiment of the present invention.

Referring to FIG. 4A, front surface 102 also includes a "J"-shaped notch 120 that extends radially inward from first outer edge 114. A first wall 122 extends axially outward from front surface 102 and is located radially inward of ratchet members 112. When assembled, first hub 54 and interior surface 48 of front cover 36 cooperate with front surface 102 and first wall 122 of spool 40 to form a chamber 124 to allow for expansion and contraction of tube 22 about first hub 54 (see FIG. 7A). The width of chamber 124 is slightly greater than the diameter of tube 22 to allow tube 22 to move freely in chamber 124, yet aids in ensuring tube 22 will not become entangled or kinked while in chamber 124. First wall 122 includes a curved arcuate portion 126 that extends axially outward from front surface 102 to intersect the top of first wall 122 and at least partially surround and cover notch 120. Tube 22 is positioned and non-movably seated in notch 120 as tube 22 is routed out of chamber 124 so that tube 22 may not enter and exit chamber while spool 40 is rotating.

Figure 4B:
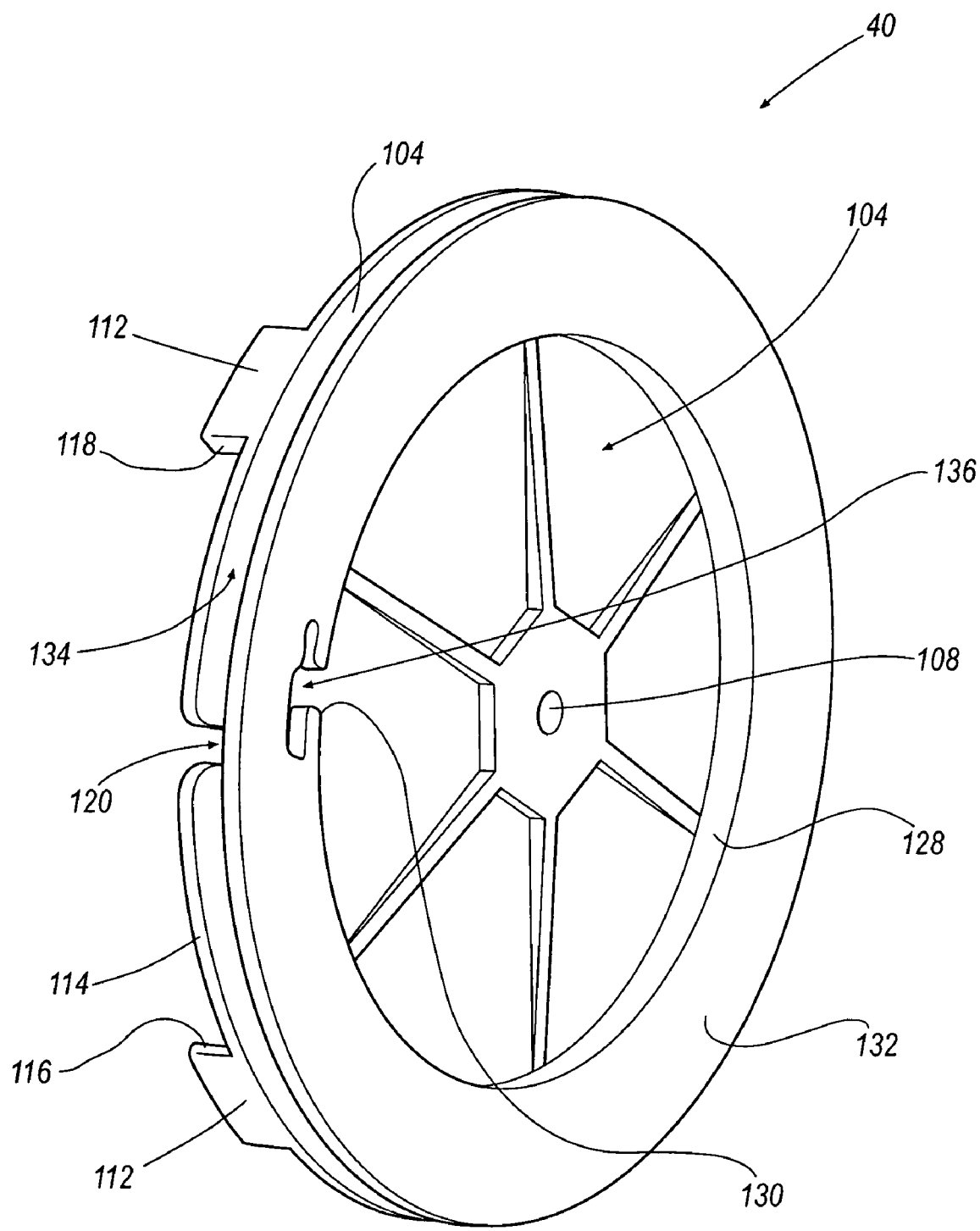

Referring to FIG. 4B, rear surface 104 of spool 40 includes a second wall 128 that extends axially outward from rear surface 104. Second wall 128 cooperates with rear surface 104 of rear cover 38 to encase spring 42. Second wall 128 is not continuous, but includes a split end 130 for attaching spring 42. Rear surface 104 also includes a flange 132 that extends radially outward from second wall 128. (Flange 132 also includes a notch 136 to provide clearance to attach spring 42 to end 130.) Flange 132 and rear surface 104 cooperatively form a spool trough 134 for storage of tube 22 prior to the extraction of tube 22 out of housing 34 through "C"-channel 88. The width of spool trough 134 is slightly greater than the diameter of tube 22 to allow tube 22 to move freely in spool trough 134, yet aids in ensuring tube 22 will not become entangled or kinked when accumulated therein.

Referring to FIGS. 2, 5A, 5B, and 7A, an embodiment of rear cover 38 is shown. Rear cover 38 includes a radially extending wall 137 having an interior surface 138, an exterior surface 140 and an outer edge 142. Rear cover 38 also includes a base 144 that extends axially outward from interior surface 138. A spindle 146 that extends axially outward from base 144 and a first shoulder 148 is positioned between base 144 and spindle 146. First shoulder 148 provides a seat for second hub 106 of spool 40 and allows spool 40 to rotate freely about base 144 and spindle 146 in housing 34. Spindle 146 includes a first tower 150 sized to pass through second hole 108 in spool 40, and a second tower 152 sized to pass through both second hole 108 and first hole 56 of front cover 36. In an embodiment, the height of first tower 150 is slightly greater than the width of second hub 106, which ensures that first hub 54 will seat on a second shoulder 154 rather than second hub 106 to prevent interference with the rotation of spool 40. Base 144 also includes a slot 156 sized to receive a portion of spring 42.

Figure 5A:
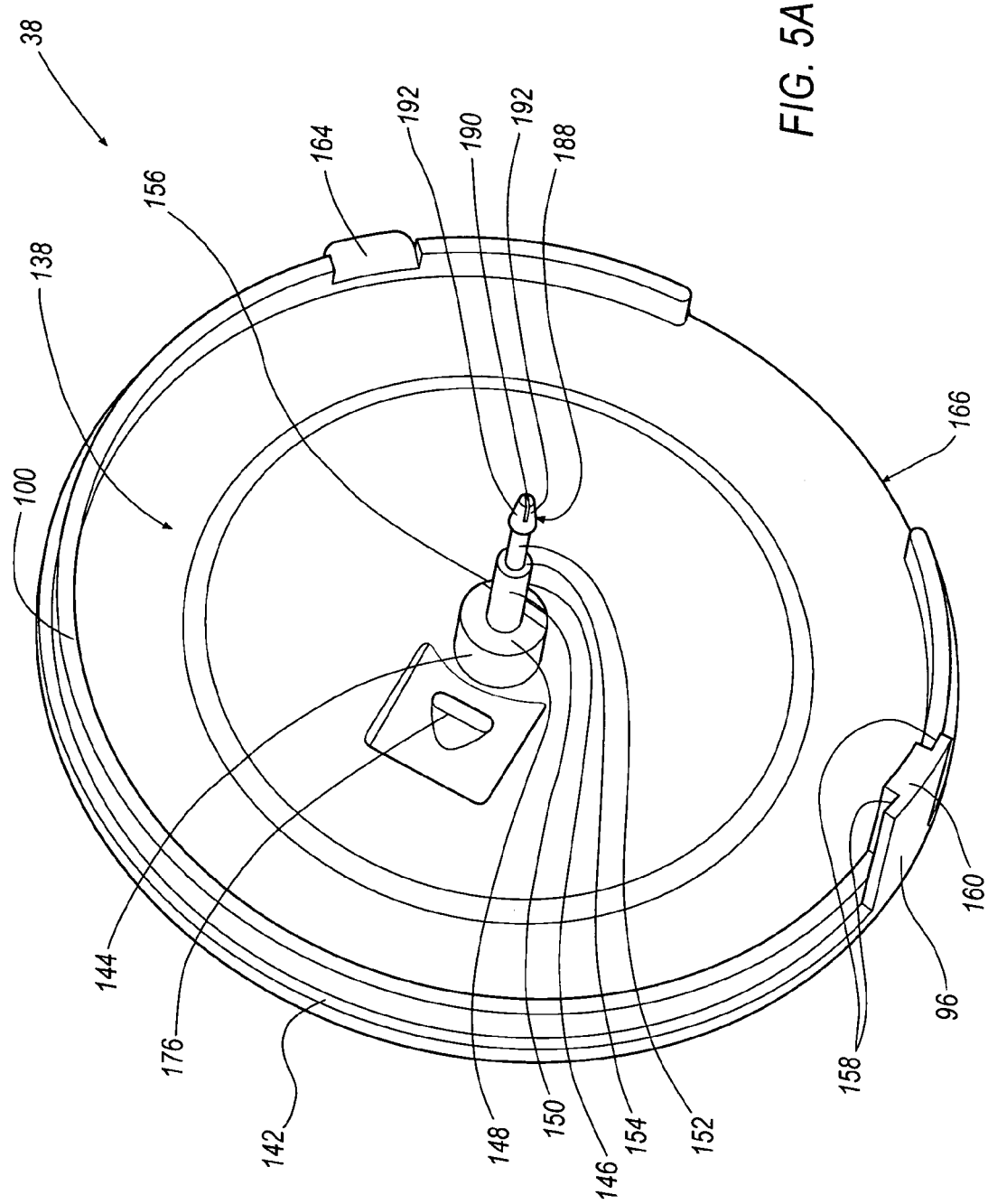
FIGS. 5A and 5B are perspective views of a rear cover according to an embodiment of the present invention.

Referring to FIG. 5A, lip 100 extends axially outward from interior surface 138 near outer edge 142. Lip 100 cooperates with outer edge 142 to engage shoulder 98 of side wall 52 during assembly of rear cover 38 to front cover 36. First tab 96 extends axially outward from lip 100 at outer edge 142 and includes a second pair of stepped surfaces 158. First tab 96 is sized to slide into opening 92 of front cover 36 and second pair of stepped surfaces 158 are sized to engage first pair of stepped surfaces 94. The engagement of first pair of stepped surfaces 94 with second pair of stepped surfaces 158 acts as a lock to prevent front cover 36 from rotating about rear cover 38. An edge 160 of first tab 96 includes a nib 162 that fits tight against tube 22 and captures tube 22 in trough 58 at opening 92 when rear cover 38 is assembled to front cover 36. Rear cover 38 also includes a second tab 164 that extends radially outward from rear cover 36. Second tab 164 intersects shoulder 98 at "C"-channel 88 to further prevent front cover 36 from rotating about rear cover 38. Rear cover 38 further includes a notch 166 at outer edge 142. Notch 166 provides clearance for latch arm 76 of front cover 36 when latch arm 76 is deflected radially inward toward first hub 54 and base 144.

In an embodiment of the invention, exterior surface 140 includes a scallop 168 for providing clearance for a curved end 170 of clip 46, and a second slot 172 for accepting a connecting end 174 of clip 46. Second slot 172 passes through rear cover 38 and interior surface 138 includes a connecting tab 176 for securing clip 46 to rear cover 38 of housing 34 (see FIGS. 5A and 5B).

Figure 2:
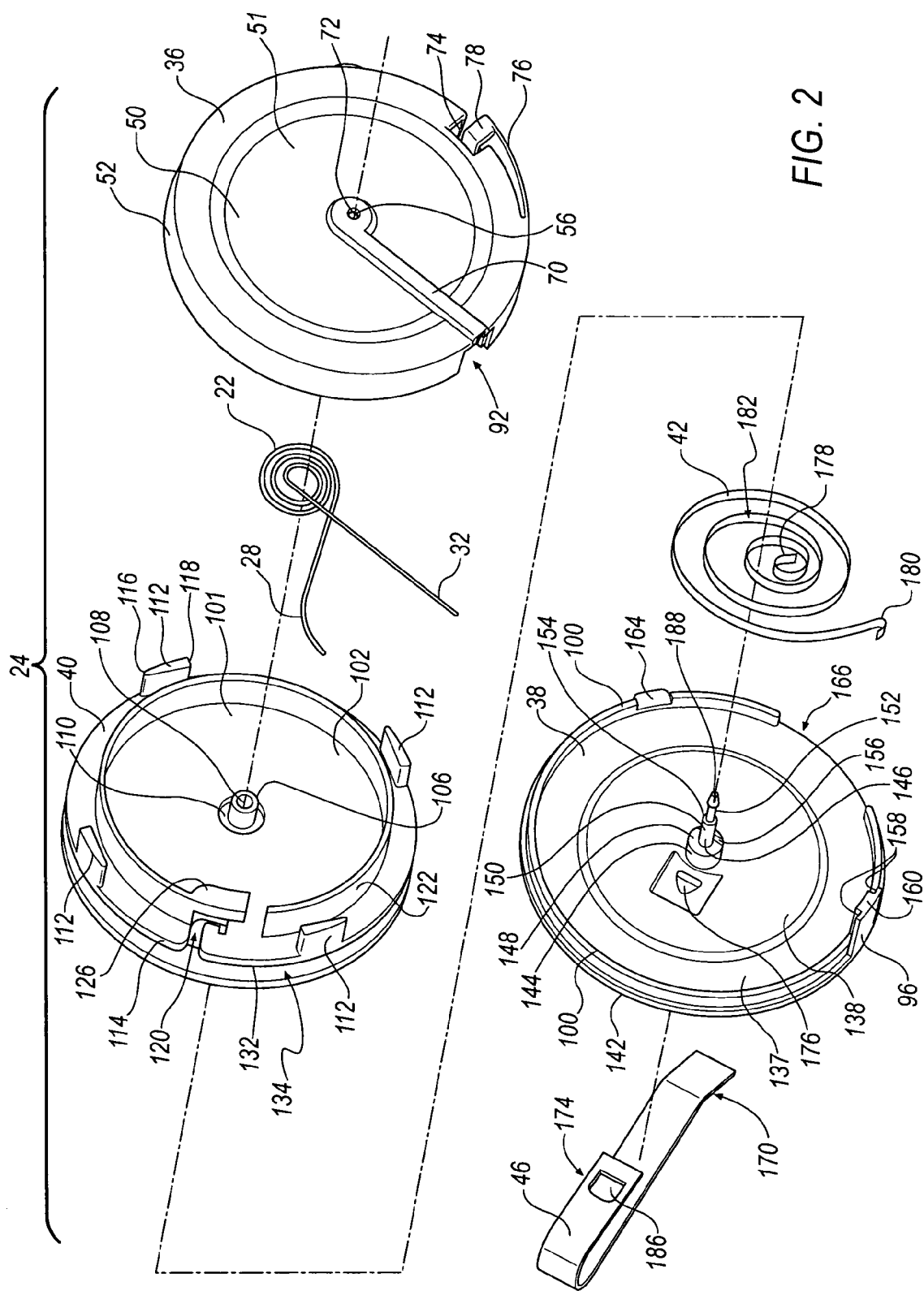
FIG. 2 is an exploded view of the retractable reel according to an embodiment of the present invention.
Figure 3A:
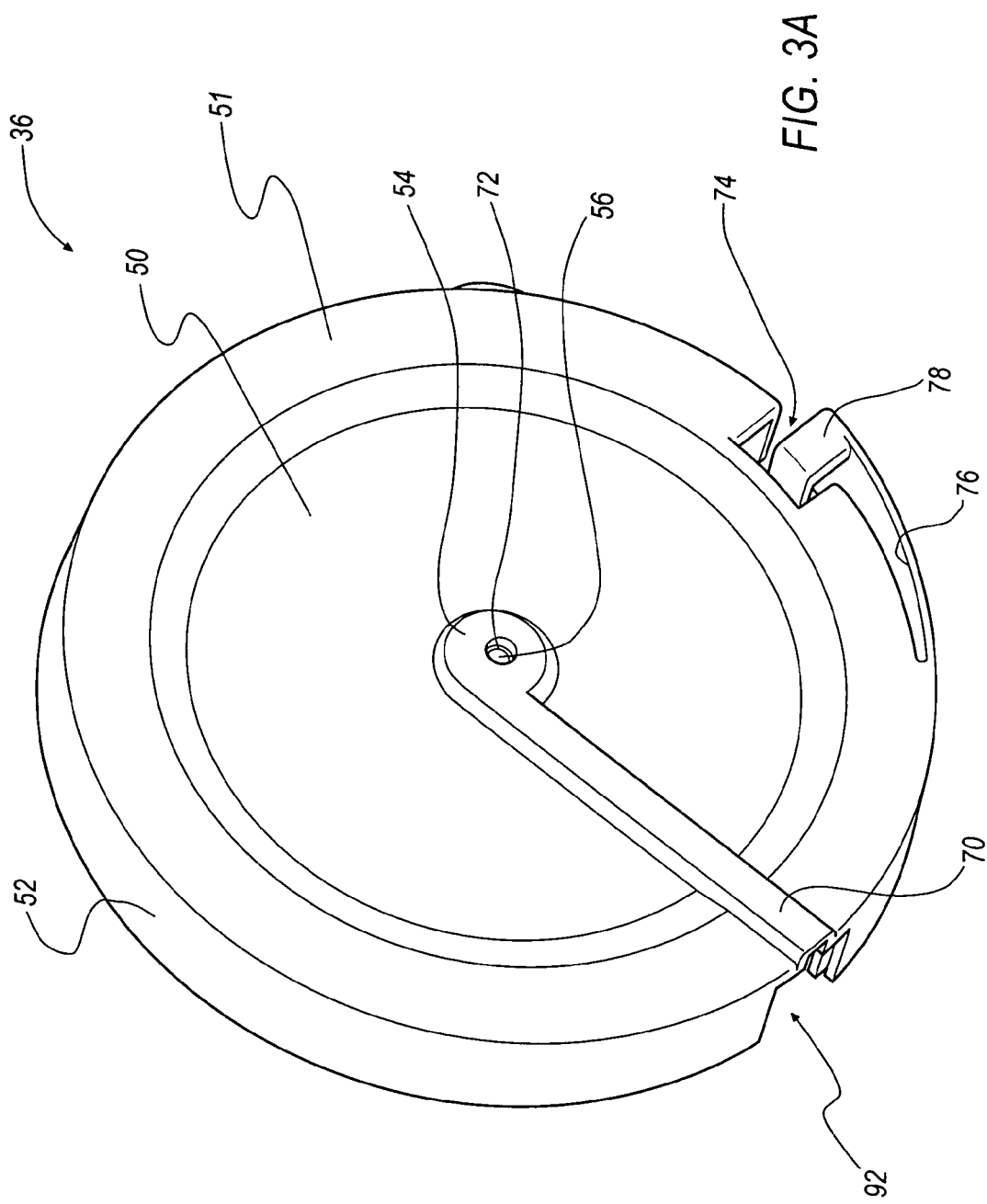
FIGS. 3A and 3B are perspective views of a front cover according to an embodiment of the present invention.
Figure 3B:
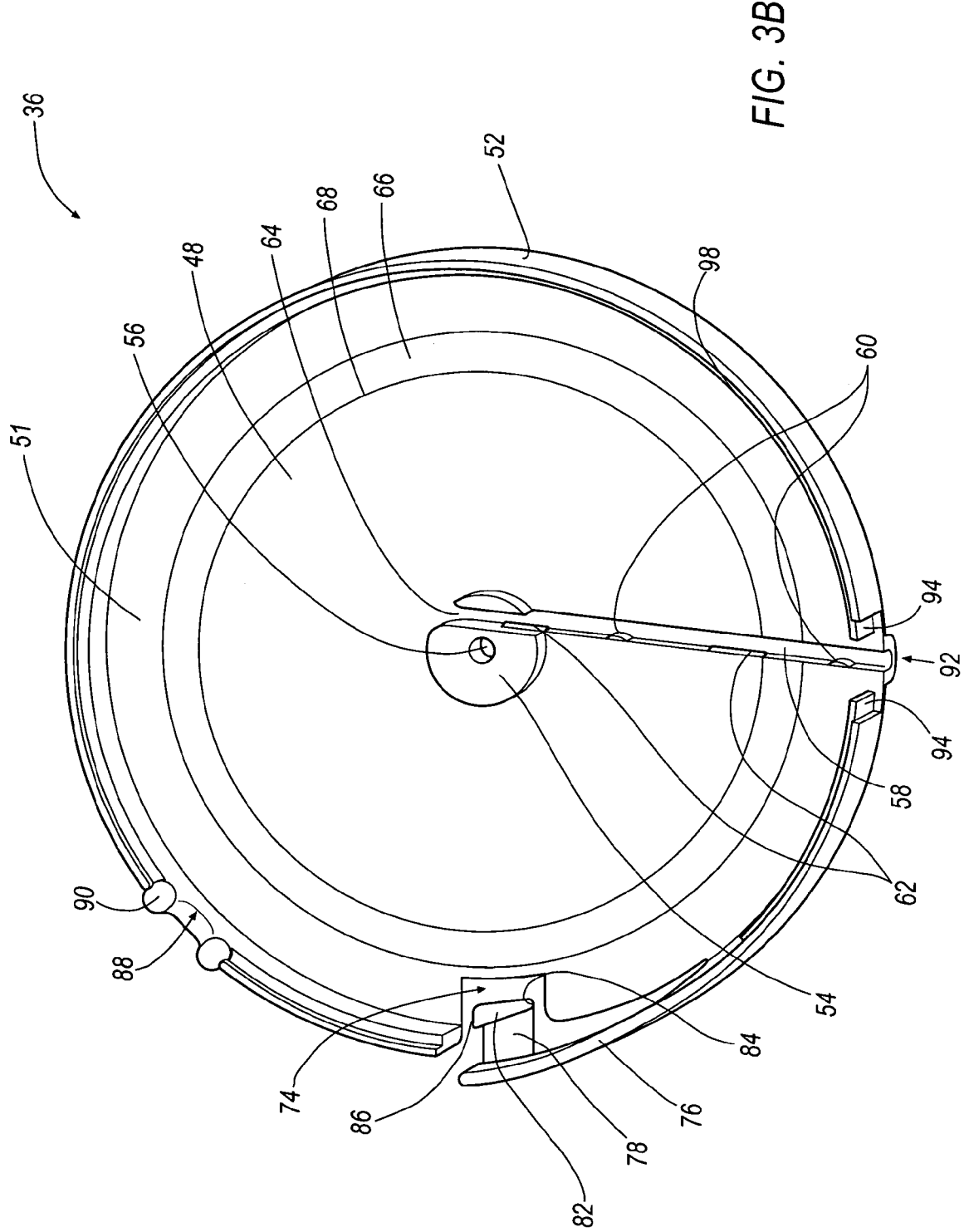
Figure 6:
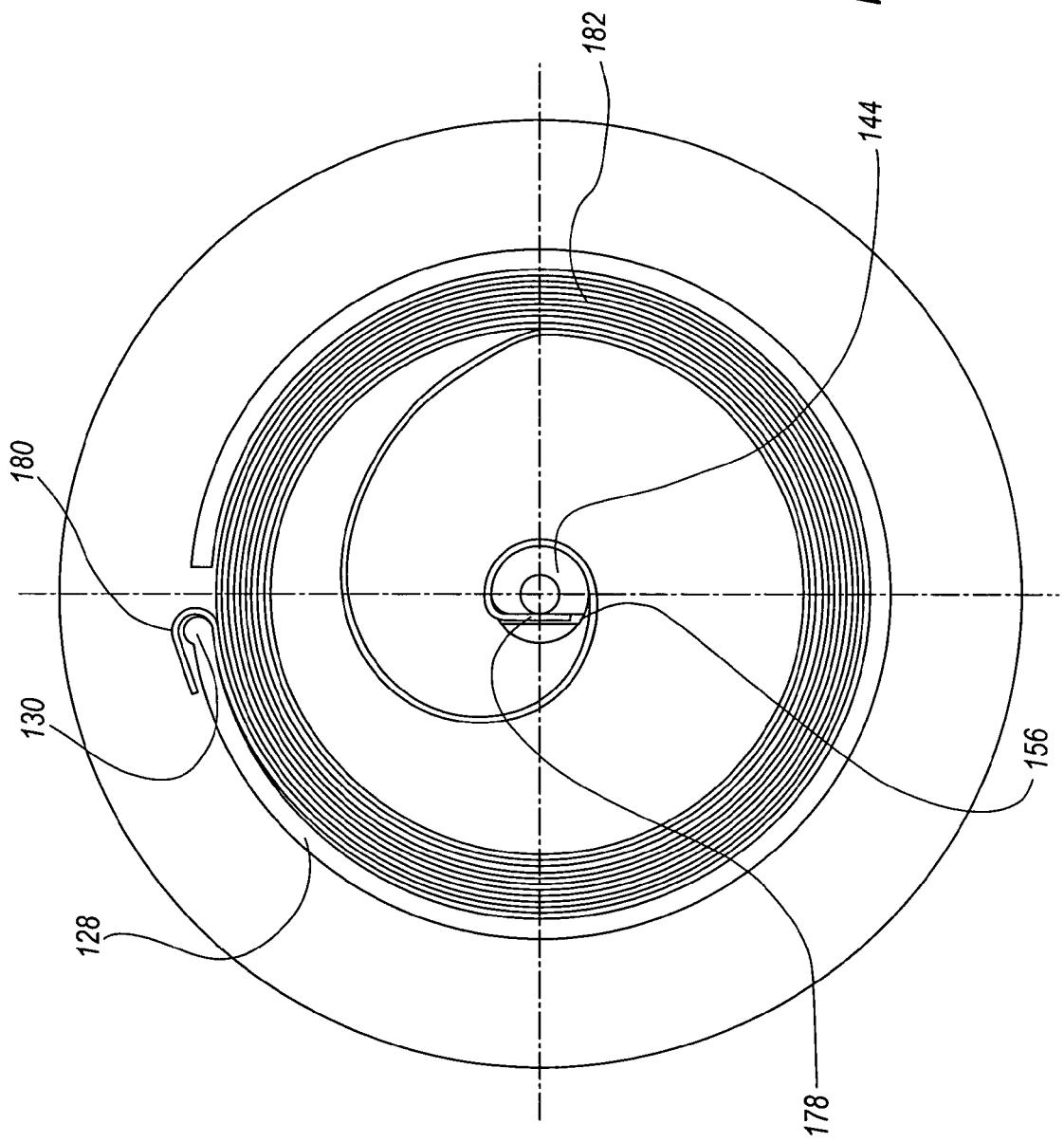
FIG. 6 is a plan view of a spring, the rear cover, and a portion of the spool according to an embodiment of the present invention.

FIGS. 2 and 6 illustrate spring 42. In an embodiment, spring 42 is a typical spiral spring with a straight portion 178 for attaching to rear cover 38 at slot 156 on base 144, a hook 180 for attaching to spool 40 at end 130 of second wall 128, and a number of coils 182. Spring 42 is located in a cavity 184 created by interior surface 138 of rear cover 38 and second wall 128 of rear surface 104 on spool 40.

Figure 5B:
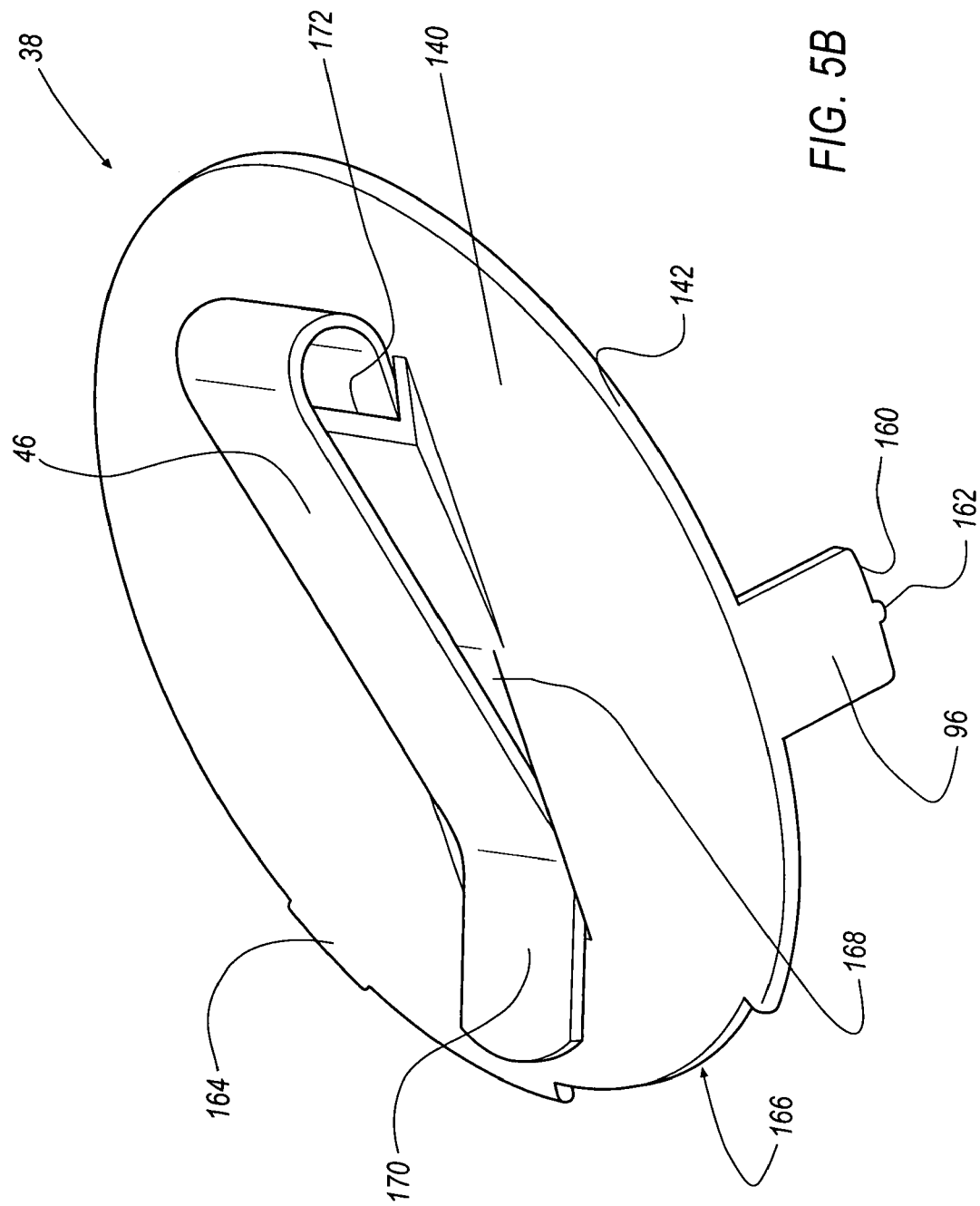

FIGS. 2 and 5B illustrate clip 46 according to an embodiment of the invention. In this embodiment, clip 46 is employed to attach retractable reel 24 to diabetic patient's 26 belt, waist band, suspender, purse strap, or the like. Curved end 170 of clip engages the belt and a flat end 174 enters second slot 172 on rear cover 38. Flat end 174 includes a cutout 186 for engaging connecting tab 176 to secure clip 46 to housing 34.

Front cover 36, rear cover 38, spool 40, spring 42, and clip 46 may be manufactured from a metallic or polymeric material, such as steel, aluminum, plastic, nylon, or acetal. Front cover 38 may be manufactured from a material that will ensure latch arm 76 maintains its resiliency during the useful life of retractable reel 24. Spool 40 may be manufactured from a material that will decrease the friction between ratchet members 112 of spool 40 and locking post 82 of front cover 36, while spool 40 is rotating about front cover 36. For example, front cover 36 may be manufactured from nylon and spool 40 may be manufactured from acetal. The combination of these materials will result in a lower frictional force at the ratchet member 112/locking post 82 interface, than would result if the components were manufactured from the same materials.

Referring again to FIGS. 2–7D, in this embodiment, retractable reel 24 is assembled in the following manner. A portion of tube 22 near second tubular end 32 is pressed snugly into trough 58 of front cover 36 at opening 92. An adequate length of second tubular end 32 remains outside of opening 92 for connection to the needle or cannula 30 prior to insertion into diabetic patient 26. As tube 22 exits trough 58, tube 22 is spirally wound in a counterclockwise direction about first hub 54. Tube 22 is continually wound about first hub 54 and itself in a spiral until first tubular end 28 is reached.

Spool 40 is then added to front cover 36 in a manner that presents ratchet members 112 of spool 40 to interior surface 48 of front cover 36, while a section of tube 22 is looped around curved arcuate portion 126 and seated in "J"-shaped notch 120 of spool 40. A section of tube 22 is non-movably seated in the lower portion of "J"-shaped notch 120 while the remainder is fed into spool trough 134. Tube 22 is then wound in a counterclockwise direction about spool trough 134 relative to front cover 36. A length of first tubular end 28 exits through "C"-channel 88 of front cover 36 for connection to insulin pump 20.

Second hole 108 of spool 40 is aligned with first hole 56 of front cover 36 and wider end 118 of at least one ratchet member 112 abuts wider end 86 of locking post 82. Hook 180 of spring 42 is attached to end 130 of second wall 128 on spool 40. Straight portion 178 of spring 42 is attached to slot 156 of base 144. Rear cover 38 is rotated in a counterclockwise direction to pre-load spring 42 prior to securing rear cover 38 to front cover 36.

Spindle 146 of rear cover 38 is aligned with second hole 108 and first hole 56. At the same time, first tab 96 of rear cover 38 is aligned with opening 92 of front cover 36 and second tab 164 of rear cover 38 is aligned with "C"-channel 88 of front cover 36. Rear cover 38 is then pressed onto spool 40 and front cover 36. Spindle 146 passes through first hole 56 and a portion of spindle 146 is proud of front cover 36. Spindle 146 may then be ultrasonically welded or "hot-staked", which causes the portion of the diameter of spindle 146 proud of front cover 36 to increase so that the new diameter of spindle 146 is greater than the diameter of first hole 56, thereby securing the assembly of rear cover 38 to spool 40 and front cover 36. Alternatively, a top 188 of spindle 146 may include a compressible gap 190 and ears 192 that pass through a second hole 108 and first hole 56 during assembly of retractable reel 24 (See FIG. 5A). As top 188 of spindle 146 exits first hole 56, gap 190 expands and forces ears 192 onto countersink 72 of front cover 36, thereby securing the assembly of rear cover 38 to spool 40 and front cover 36. Other fastening means may be employed in conjunction with or instead of the configuration described above. For example, glue may be used to assemble rear cover 38 to front cover 36 or another snap together feature could be employed.

As will be appreciated, first tubular end 28 will be connected to insulin pump 20 and second tubular end 32 will be connected to the needle or cannula 30. The connection of tube 22 in this manner ensures that the retractable length of tube 22 is connected to insulin pump 20 and diabetic patient 26 has freedom to position insulin pump 20 for comfortable reading by removing the proper length of tube 22 from housing 34. To ensure that the connection is made in this manner, tube 22 may have opposite female and male connectors fitted to either end that correspond to the correct fitting on insulin pump 20 and the needle or cannula 30. This will eliminate any confusion on which side of tube 22 is to be connected to insulin pump 20 and the needle or cannula 30.

Retractable reel 24 is operated by pulling first tubular end 28 out of "C"-channel 88. As tube 22 is pulled from housing 34, spool 40 is rotating in a counterclockwise direction relative to front cover 36. Spool 40 is releasing tube 22 as it is rotated counterclockwise as well as loading spring 42 to rotate spool 40 in a clockwise direction. Tube 22 is non-movably seated in the lower portion of the "J"-shaped notch 120 to aid diabetic patient 26 in extracting tube 22. The lower portion of the "J"-shaped notch 120 provides a pull point on spool 40. As tube 22 is extracted, tube 22 is also pulling spool 40 in a counterclockwise direction.

Referring now to FIGS. 8A–8E, as will be appreciated, the extractable length of tube 22 used in the operation of retractable reel 24 will be retained in spool trough 134. Tube 22 will be non-moveably seated in "J"-shaped notch 120 on spool 40 and tube 22 may not enter or leave chamber 124. Chamber 124 will house a length of tube 22 that allows spool 40 to rotate freely and ensure tube 22 remains free of kinks. Tube 22 will uncoil from itself, while remaining in chamber 124, as tube 22 is extracted from spool trough 134 and spool 40 is rotated in a counterclockwise direction (see FIGS. 8E–8A). When tube 22 is retracted into spool trough 134, tube 22 will uncoil within chamber 124 until complete length of tube 22 is uncoiled, then tube 22 will coil about itself in a reverse spiral. (see FIGS. 8A–8E). The continual coiling-uncoiling-coiling of tube 22 about itself within chamber 124 allows retractable reel 24 to operate without a rotatable coupling, yet ensures that tube 22 will not become kinked or otherwise impede the flow of insulin through tube 22.

Now referring to FIGS. 9A, 9B, 10A, and 10B, in another embodiment of the invention, tube 22 contained in chamber 124 may operate in this manner. Tube 22 will uncoil from itself, while remaining in chamber 124, as tube 22 is extracted from spool trough 134 and spool 40 is rotated in a counterclockwise direction (see FIGS. 9B and 10A). When tube 22 is retracted into spool trough 134, tube 22 in chamber 124 will recoil onto itself (see FIGS. 9A and 10B). The spiral expansion and contraction of tube 22 about itself within chamber 124 allows retractable reel 24 to operate without a rotatable coupling, yet ensures that tube 22 will not become kinked or otherwise impede the flow of insulin through tube 22. This particular embodiment may prove advantageous when there is an excess amount of tube 22 available in a particular infusion set and storage of the excess tube 22 is required.

Figure 11A:
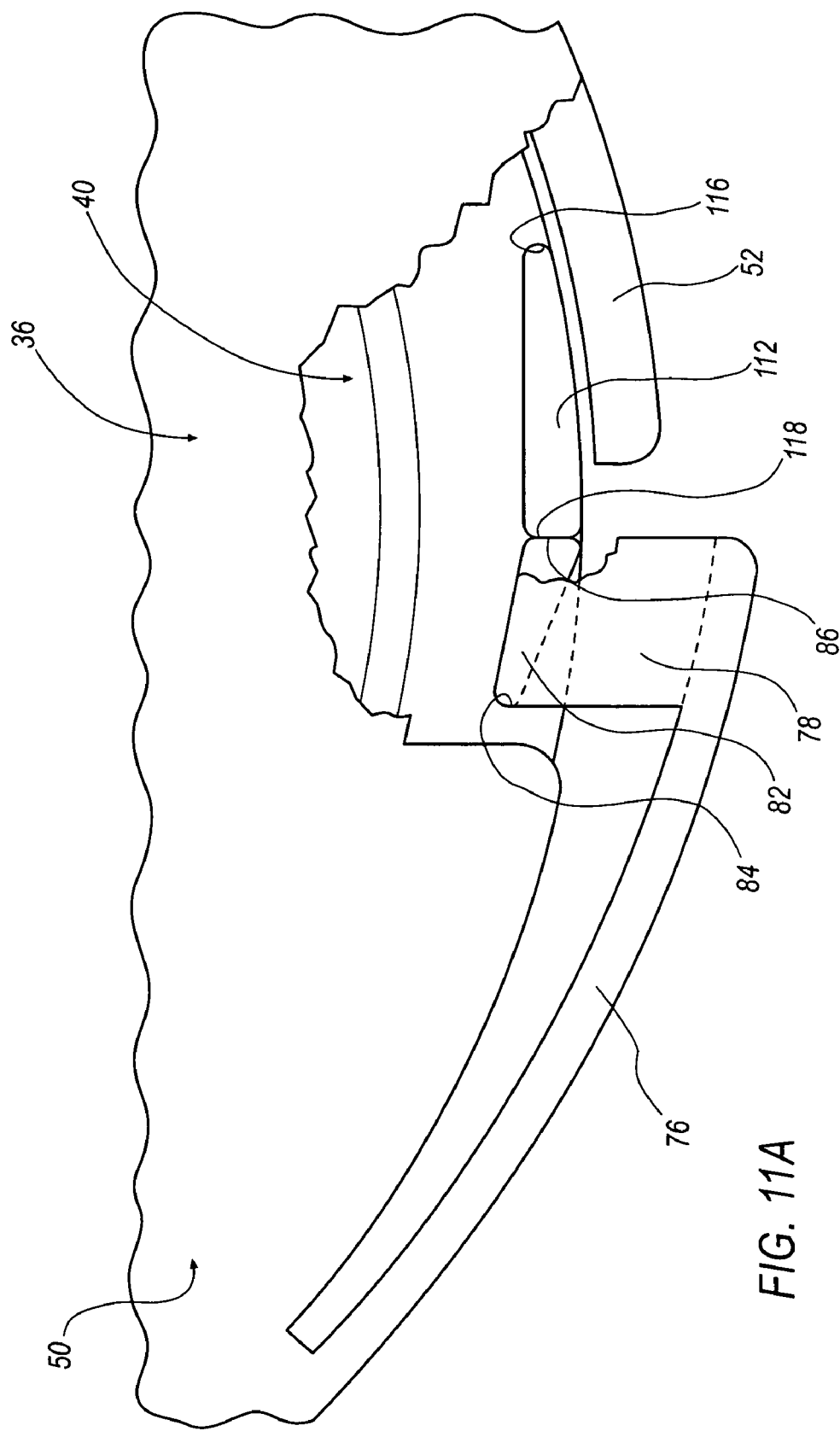
Figure 11C:
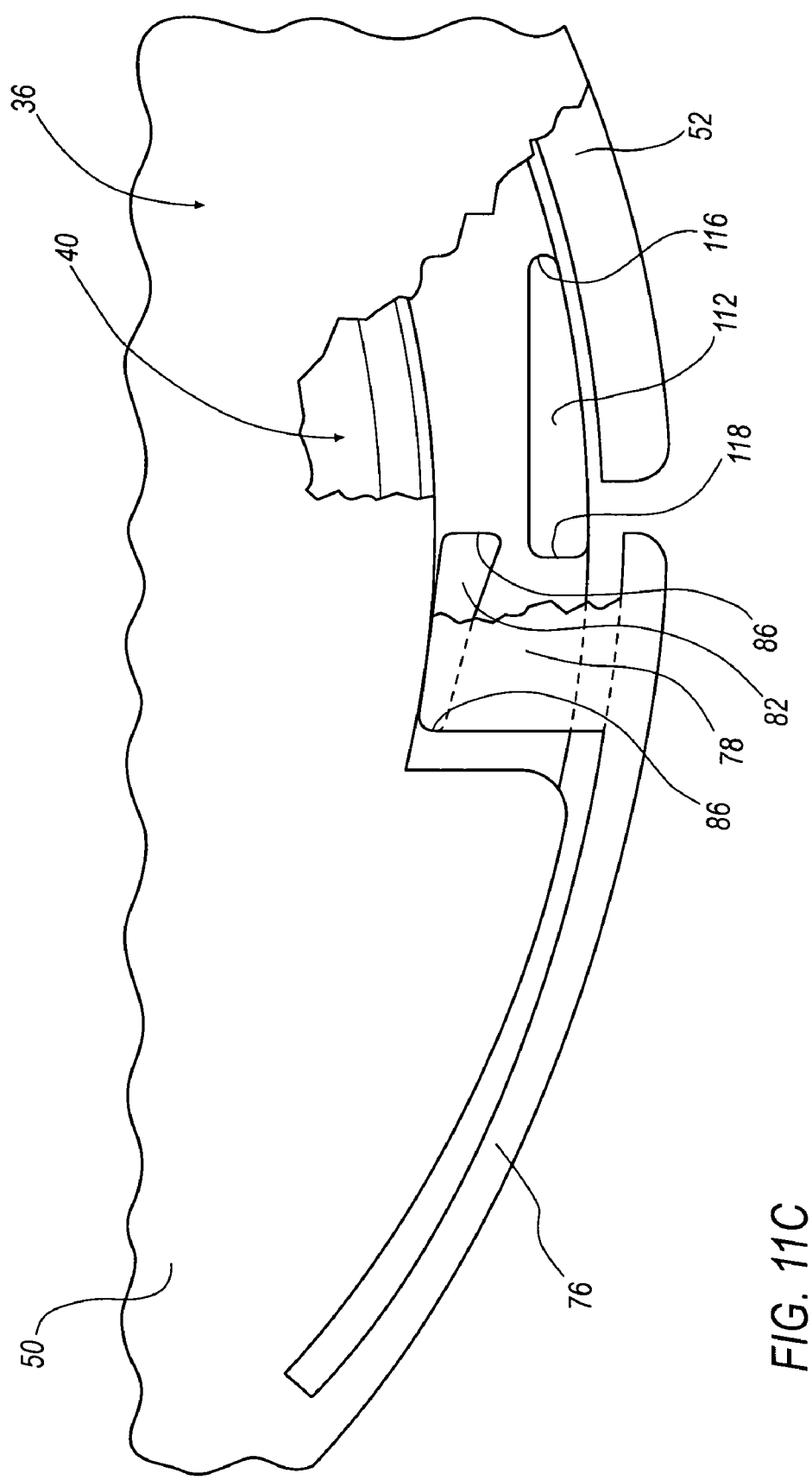

Now referring to FIGS. 11A, 11B, and 11C, in this particular embodiment, four ratchet members 112, generally triangular in shape, are employed and are spaced at 90° intervals on front surface 102 of spool 40. The use of four ratchet members 112 allows for extraction and retraction of tube 22 in relatively small increments to limit the amount of tube 22 outside housing 34 and help reduce the risk of snagging tube 22 on objects. As spool 40 is rotated in a counterclockwise direction, pointed end 116 of ratchet member 112 approaches pointed end 84 of locking post 82. Ratchet members 112 are positioned on spool 40 such that when pointed end 116 engages pointed end 84, pointed end 116 forces pointed end 84 radially inward toward first hub 54 and second hub 106. This camming action deflects locking post 82 out of the travel path of ratchet members 112 and allows ratchet members 112 to pass by locking post 82, spool 40 to rotate freely, and tube 22 to be readily pulled from housing 34 as needed. In this particular embodiment, angles of pointed ends 84 and 116 are small or shallow so that a very small amount of force is required for pointed end 116 of ratchet members 112 to deflect pointed end 84 of locking post out of the path of ratchet members 112.

When the desired length of tube 22 has been removed from housing 34, spring 42 will be loaded to rotate spool 40 in a clockwise direction and retract tube 22 into housing 34. To prevent the unwanted retraction of tube 22, the first, wider end 86 of locking post 82 will engage the second, wider end 118 of ratchet member 112 and prevent spool 40 from rotating in a clockwise direction. The desired length of tube 22 will be locked in place and diabetic patient 26 can perform the needed operations with insulin pump 20.

When retraction of tube 22 into reel is desired, diabetic patient 26 can move latch arm 76 radially inward toward first hub 56. Deflecting latch arm 76 radially inward also moves locking post 82 radially inward, thus removing the engagement of wider end 86 of locking post 82 with wider end 118 of ratchet member 112. Locking post 82 is now out of the travel path of ratchet member 112. Spool 40 is able to rotate freely in a clockwise direction and retract tube 22 in housing 34. Spool 40 will rotate freely until diabetic patient 26 releases latch arm 76 allowing latch arm 76 to move radially outward to its normal non-deflected position. Locking post 82 will be in the travel path of ratchet member 112 such that wider end 86 of locking post 82 will engage wider end 118 of ratchet member 112. Also, a stop (not shown) may be added to tube 22 which may be used to engage arcuate surface 90 of "C"-channel 88 to inhibit the entire tube 22 from entering housing 34. Generally, retractable reel 24 will be manufactured with latch arm 76 at the bottom of housing 34 when positioned on diabetic patient 26 to allow retractable reel 24 to be operated by either right handed or left handed diabetic patients 26 with a natural hand motion by their fingers.

As will be appreciated, the force required to pull tube 22 from housing 34 may be relatively low so that in the event tube 22 does become snagged on a doorknob, stair banister, chair arm or the like, tube 22 will be extracted from housing 34 rather than cause needle or cannula 30 to be removed from the diabetic patient 26. However, the force on tube 22 and housing 34 may be high enough to alert diabetic patient 26 to a problem before the full length of tube 22 is extracted from housing 34.

As will be appreciated, retractable reel 24 may be manufactured as thin as possible so that it can easily be hidden under clothing. Retractable reel 24 is designed to be as flush to a diabetic patient's body 26 as possible with tube 22 both entering and exiting housing 34 perpendicular to spindle 146. Retractable reel 24 should be user friendly and robust because of the many types of users of retractable reel 24 including small children, active individuals, and older patients. Retractable reel 24 should also be low cost as well because retractable reel 24 may be disposable or recyclable after three to seven days of use.

Figure 12:
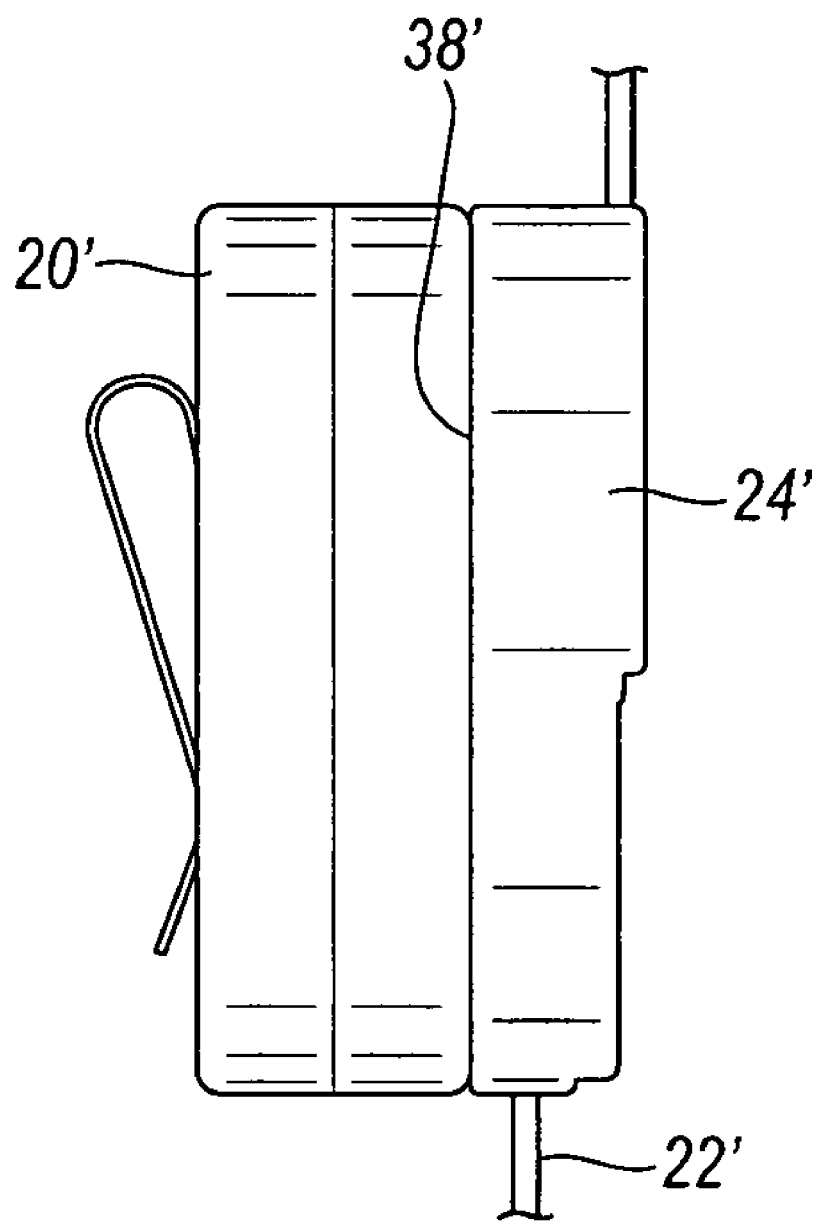
FIG. 12 is an elevation view of a medical system, including the retractable reel and the insulin pump, according to another embodiment of the present invention.

FIG. 12 illustrates another embodiment of the invention. In this embodiment, retractable reel 24' can be attached directly to insulin pump 20', thus eliminating the need for a separate clip 46. For example, the case of insulin pump 20' can be molded to accept a molded clip (not shown) on rear cover 38' of retractable reel 24'. This embodiment allows for simultaneous operation of retractable reel 24' while returning insulin pump 20' to the normal operating location, usually the waist area of diabetic patient 26. Tube 22' can be retracted at the same time as insulin pump 20' and retractable reel 24' are returned to the waist. This will aid in ensuring tube 22' is retracted quickly and lessens the chance that tube 22' could become snagged on an object.

The retractable reel 24 has been fully shown and described with the use of tube 22. It is important to note, however, that retractable reel 24 may be used with any type of elongated flexible member including, but not limited to, telephone cords, electrical cords, cable, or the like.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A retractable reel comprising:
 a housing including a front cover and a rear cover, the rear cover including a first opening and the front cover including a second opening, a trough extending radially inward from the second opening to a center of the front cover, the trough including at least one tab and at least one dimple, and a resiliently deflectable latch arm;
 a spool including a wall that extends axially outward from a front surface of the spool, the spool rotatably supported within the housing and positioned such that the front surface, the wall and the front cover cooperatively define a chamber therebetween, the spool further including at least one ratchet member selectively engaged by the resiliently deflectable latch arm to prevent rotation of the spool in a winding direction;
 a spring including a first end engaging the rear cover and a second end engaging the spool for rotatively biasing the spool in the winding direction;
 a flexible member including a first portion that passes through the first opening and is spirally wound upon the spool and a second portion that passes through the second opening, the second portion having a first section secured to the housing in the trough by the tab and dimple, and a second section spirally wound in the chamber; and
 whereby the first portion of the flexible member may be selectively unwound from the spool as the second portion of the flexible member is unwound and wound about itself within the chamber or wound upon the spool as the second portion of the flexible member is unwound and wound about itself within the chamber.

2. The retractable reel of claim 1, wherein the resiliently deflectable latch arm includes a locking post configured to allow passage of the ratchet member during rotation on the spool in an unwinding direction and to selectively engage and prevent rotation of the spool in the winding direction.

3. The retractable reel of claim 2, wherein the resiliently deflectable latch arm is cantilevered over the ratchet member, the locking post and the ratchet member being configured to cause a radially inward deflection of the resiliently deflectable latch arm during engagement with the ratchet member to allow passage of the ratchet member and rotation of the spool.

4. The retractable reel of claim 1 further including a plurality of ratchet members.

5. The retractable reel of claim 1, wherein the spool includes a trough sized to collect the first portion of the flexible member and a recess sized to receive the second portion of the flexible member.

6. The retractable reel of claim 5, wherein the trough is slightly larger than the width of the flexible member.

7. The retractable reel of claim 1, wherein first portion of the flexible member is unwound from the spool in a first direction and the second portion of the flexible member is unwound and wound within the chamber in the first direction.

8. The retractable reel of claim 7, wherein the first portion of the flexible member is wound onto the spool in a second direction and the second portion of the flexible member is unwound and wound within the chamber in the second direction.

9. The retractable reel of claim 1, wherein the flexible member includes a third, non-movable portion between the first and second portions.

10. The retractable reel of claim 1, wherein the flexible member is one of tubing and wire.

11. The retractable reel of claim 1, wherein the first and second portions of the flexible member include respective first and second tubular ends.

12. The retractable reel of claim 1 further including a clip secured to the housing.

13. A medical system, comprising:
an insulin pump; and
a retractable reel, the retractable reel including:
  a housing having a a front cover, a rear cover, the rear cover including a first opening and the front cover including a second opening, a trough extending radially inward from the second opening to a center of the front cover, the trough including at least one tab and at least one dimple and a resiliently deflectable latch arm;
  a spool having a wall that extends axially outward from a front surface of the spool, the spool rotatably supported within the housing and positioned such that the front surface, the wall, and the front cover cooperatively define a chamber therebetween, the spool further including at least one ratchet member selectively engaged by the resiliently deflectable latch arm to prevent rotation of the spool in a winding direction;
  a spring including a first end engaging the rear cover and a second end engaging the spool for rotatively biasing the spool in the winding direction;
  a length of flexible tubing that includes a first portion that passes through the first opening and is spirally wound upon the spool and a second portion that passes through the second opening, the second portion having a first section secured to the housing in the trough by the tab and dimple, and a second section spirally wound in the chamber;
  a clip secured to the housing; and
  whereby the first portion of the flexible tubing may be selectively unwound from the spool as the second portion of the flexible tubing is unwound and wound about itself within the chamber or wound upon the spool as the second portion of the flexible tubing is unwound and wound about itself within the chamber.

14. The medical system of claim 13, wherein the resiliently deflectable latch arm includes a locking post configured to allow passage of the ratchet member during rotation on the spool in an unwinding direction and to selectively engage and prevent rotation of the spool in the winding direction.

15. The medical system of claim 14, wherein the resiliently deflectable latch arm is cantilevered over the ratchet member, the locking post and the ratchet member being configured to cause a radially inward deflection of the resiliently deflectable latch arm during engagement with the ratchet member to allow passage of the ratchet member and rotation of the spool.

16. The medical system of claim 13 further including a plurality of ratchet members.

17. The medical system of claim 13, wherein the spool includes a trough sized to collect the first portion of the flexible tubing and a recess sized to receive the second portion of the flexible tubing.

18. The medical system of claim 17, wherein the trough is slightly larger than the width of the flexible tubing.

19. The medical system of claim 13, wherein the first portion of the flexible tubing is unwound from the spool in a first direction and the second portion of the flexible tubing is unwound and wound within the chamber in the first direction.

20. The medical system of claim 19, wherein the first portion of the flexible tubing is wound onto the spool in a second direction and the second portion of the flexible tubing is unwound and wound within the chamber in the second direction.

21. The medical system of claim 13, wherein the flexible tubing includes a third, non-movable portion between the first and second portions.

22. The medical system of claim 13, wherein the first and second portions of the flexible tubing include respective first and second tubular ends.

23. The medical system of claim 13, wherein the retractable reel is secured to the insulin pump.

* * * * *